US006693190B1

(12) United States Patent
Ranganathan et al.

(10) Patent No.: US 6,693,190 B1
(45) Date of Patent: Feb. 17, 2004

(54) ENHANCED RELAXIVITY MONOMERIC AND MULTIMERIC COMPOUNDS

(75) Inventors: Ramachandran S. Ranganathan, Princeton, NJ (US); Radhakrishna Pillai, Kendall Park, NJ (US); Peter C. Ratsep, Hamilton Square, NJ (US); Rajesh Shukla, Lawrenceville, NJ (US); Michael F. Tweedle, Princeton, NJ (US); Xun Zhang, Kendall Park, NJ (US)

(73) Assignee: Bracco International B.V., Amsterdam (NL)

( * ) Notice: Subject to any disclaimer, the term of this patent is extended or adjusted under 35 U.S.C. 154(b) by 1,508 days.

(21) Appl. No.: 08/241,253

(22) Filed: May 11, 1994

(51) Int. Cl.[7] .................... C07D 257/02; C07D 493/10; C07D 405/14; C07F 9/6524

(52) U.S. Cl. ....................... 540/465; 540/474

(58) Field of Search .................. 540/465, 474

(56) References Cited

U.S. PATENT DOCUMENTS

| | | | | |
|---|---|---|---|---|
| 4,678,667 A | | 7/1987 | Meares et al. ............... | 424/85 |
| 4,880,008 A | | 11/1989 | Lauffer ....................... | 128/654 |
| 4,885,363 A | * | 12/1989 | Tweedle et al. ............ | 540/465 |
| 4,899,755 A | | 2/1990 | Lauffer et al. ............. | 128/654 |
| 4,923,985 A | | 5/1990 | Gansow et al. ............ | 540/474 |
| 5,049,667 A | | 9/1991 | Schaefer et al. ........... | 540/474 |
| 5,053,503 A | | 10/1991 | Dean et al. ................ | 540/474 |
| 5,247,075 A | * | 9/1993 | Parker et al. .............. | 540/474 |
| 5,271,927 A | | 12/1993 | Parker et al. .............. | 424/9 |
| 5,277,895 A | | 1/1994 | Platzek et al. ............. | 424/9 |

FOREIGN PATENT DOCUMENTS

| | | |
|---|---|---|
| EP | 071564 | 9/1983 |
| EP | 186947 | 7/1986 |
| EP | 255471 | 2/1988 |
| EP | 353450 | 2/1990 |
| EP | 0365412 | 4/1990 |
| EP | 374947 | 6/1990 |
| EP | 0382583 | 8/1990 |
| EP | 392423 | 10/1990 |
| EP | 466200 | 1/1992 |
| EP | 481420 | 4/1992 |
| EP | 485045 | 5/1992 |
| EP | 0485045 | 5/1992 |
| EP | 565930 | 10/1993 |
| WO | 89/05802 | 6/1989 |
| WO | 89/11475 | 11/1989 |
| WO | 90/12050 | 10/1990 |
| WO | 92/04336 | 3/1992 |
| WO | 92/04919 | 4/1992 |
| WO | 92/09884 | 6/1992 |
| WO | 92/12978 | 8/1992 |
| WO | 93/02045 | 2/1993 |

OTHER PUBLICATIONS

Hashiguchi et al., Study on Gadolinium Complexes Based on Polysaccharide Derivatives as a Contrast Agent for MRI, *The Chem. Soc. of Japan* (5), p. 521–527 (1993).

Hindre et al., Tetra–p–aminophenylporphyrin Conjugated with Gd–DTPA: *Tumor–specific Contrast Agent for MR Imaging, JMRI*, p. 59–65 (1993).

Powell et al., Magnetic–Field–Dependent Electronic Relaxation of $Gd^{3+}$ in Aqueous Solutions of the Complexes $[Gd(H_2O)_8]^{3+}$, [Gd(propane–1,3–diamine–N,N,N', N'–tetraacetate)$(H_2O)_2]^-$, and [Gd(N,N'–bis[(N–methylcarbamoyl)methyl]–3–azapentane–1,5–diamine–3,N, N'–triacetate)$(H_2O)$]of Interest in Magnetic–Resonance Imaging, *Helvetica Chimica Acta* (vol. 76) p. 2129–2146 (1993).

Kang, et al., Synthesis, Characterization and Crystal Structure of the Gadolinium(III) Chelate of (1R,4R,7R)–α, α'α''–Trimethyl–1,4,7,10–tetraazacyclododecane–1,4,7–triacetic acid (DO3MA), *Inorg. Chem.* 32, p. 2912–2918 (1993).

Kumar et al., Ligand Basicity and Rigidity Control Formation of Macro–cyclic Polyamino Carboxylate Complexes of Gadolinium (III), *Inorg. Chem.*, 32, p. 4193–4199 (1993).

Seri et al., Abstract, Gadolinium complex of 1,4,7,10–tetraazacyclodo–decane–1,4,7,10–α,α',α'',α'''–tetrakis(methylacetic acid) as magnetic resonance imaging agent, *Chemical Abstracts*, vol. 117:43666y (1992).

(List continued on next page.)

*Primary Examiner*—Richard L. Raymond
*Assistant Examiner*—C. Styles
(74) *Attorney, Agent, or Firm*—Kramer, Levin, Naftalis & Frankel LLP

(57) ABSTRACT

Metal chelates capable of exhibiting an immobilized relativity between about 60 and 200 $mM^{-1}s^{-1}$/metal atom are useful as magnetic resonance imaging agents. Additionally, a compound which is useful as a metal-chelating ligand has the following formula:

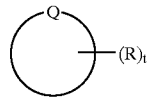

wherein

Q is a 4- to an 8-membered carbocyclic ring which may be fully or partially saturated;

t is an integer from 2 to 16;

each R group is independently hydrogen, —OH, —$CH_2$—A, —O$CH_2$CH(OH)$CH_2$—A or a functional group capable of forming a conjugate with a biomolecule, provided that at least two of the R groups are selected from —$CH_2$—A or —O$CH_2$CH(OH) $CH_2$—A; and A is a moiety capable of chelating a metal atom.

14 Claims, No Drawings

OTHER PUBLICATIONS

Pikul et al., (1R,2R)–(+)– and (1S,2S)–(–)1,2–Diphenyl–1, 2–ethylene–diamine, *Organic Syntheses* (*1992*) *71*, pp. 22–27.

Geraldes et al., Nuclear Magnetic Relaxation Dispersion Profiles of Aqueous Solutions of a Series of Gd(NOTA) Analogs, *Magnetic Resonance in Medicine, 27*, p. 284–295 (1992).

Schaefer et al., A New Macrocyclic MRI Contrast Agent: Gd MCTA Complex, *Magnetic Resonance in Medicine, 22*, p. 238–241 (1991).

Neumann et al., The Stereoselective Synthesis of Functionalized Vicinal Diamine Systems by the Double Allylation Reactions of "Protected" 1,2–Bis–Imine Precursors, *Tetrahedron Letters*, vol. 32, No. 42, p. 5865–5868 (1991).

Felder et al., Abstract, Preparation of N–carboxymethyl–1, 4,7,10–tetraazacyclododecanes and analogs for use in metal chelate contrast agents, *Chemical Abstracts*, vol. 112:77234y(1990).

Roskamp et al., Convenient Routes to Vicinal Diamines. Coupling of Nitriles of N–(Trimethylsilyl)imines Promoted by $NbCl_4(THF)_2$, *J. Am. Chem. Soc., 109*, p. 3152–3154 (1987).

Goto et al., Stoichiometry and Kinetics of Base–Promoted Disproportionation with Concomitant Ligand Oxidation of Tetracyano(1,2–diamine)ferrate(III), *Inorg. Chem., 24*, p. 582–587 (1985).

Fraenkel, et al., Efficient One–Step Synthesis of a Cis Vicinal Tertiary Diamine and Its Complexation to a Lithium Carbanion Salt, *J. Org. Chem., 49*, p. 1314–1316 (1984).

Brittain et al., Luminescence and NMR Studies of the Conformational Isomers of Lanthanide Complexes with an Optically Active Polyaza Polycarboxylic Macrocyle, *Inorg. Chem. 23*, p. 4459–4466 (1984).

Stetter et al., Darstellung Und Komplexbildung von Polyazacyclo–alkan–N–Essigsauren, *Tetrahedron*, vol. 37, p. 767–772 (1981).

Goto et al., Circular Dichroism Spectra of Some Transition Metal Complexes with (1R,2R)–1,2–Cyclopentanediamine, *Bul. of the Chemical Society of Japan, 52* (*9*), p. 2589–2595 (1979).

* cited by examiner

ENHANCED RELAXIVITY MONOMERIC AND MULTIMERIC COMPOUNDS

BRIEF DESCRIPTION OF THE INVENTION

In accordance with the present invention, novel monomeric and multimeric compounds having enhanced relaxivities are provided. These compounds are useful, for example, as metal-chelating ligands. The compounds are also useful in the form of metal complexes as diagnostic contrast agents. When the metal in the complex is paramagnetic, the diagnostic contrast agents are especially suitable for magnetic resonance imaging (MRI).

In one embodiment of the invention, certain specific compounds comprise a tetraazacyclododecane macrocycle, and are represented by the formula I:

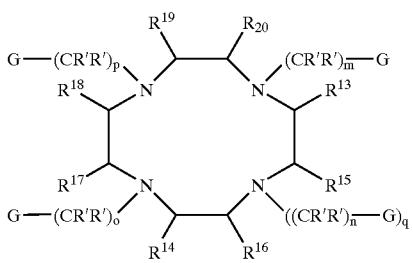

wherein
each m, n, o and p is independently 1 or 2;
q is 0 or 1;
each G is independently —COOR", —P(O)(OR")$_2$, —P(O)(OR")(R") or —C(O)N(R")$_2$;
each R' is independently hydrogen or alkyl, alkoxy, cycloalkyl, hydroxyalkyl or aryl, each of which is optionally substituted, or a functional group capable of forming a conjugate with a biomolecule or of forming a multimer of said compound of formula I;
each R" is hydrogen;
each $R^{13}$ through $R^{20}$ is independently hydrogen, alkyl, hydroxyalkyl, alkoxyalkyl or a functional group capable of forming a conjugate with a biomolecule or of forming a multimer of said compound of the formula I;
or $R^{13}$ together with $R^{15}$, and $R^{17}$ together with $R^{18}$, independently form, together with the carbon atoms in the tetraazacyclododecane macrocycle to which they are attached, a fused fully or partially saturated non-aromatic cyclohexyl ring which may be unsubstituted or substituted by one or more halogen, alkyl, ether, hydroxy or hydroxyalkyl groups, and which may be further fused to a carbocyclic ring, or $R^{13}$ and $R^{15}$ are each hydrogen and $R^{17}$, together with $R^{18}$, forms a fused fully or partially saturated non-aromatic cyclohexyl ring as defined above, or $R^{13}$, together with $R^{15}$, forms a fused fully or partially saturated non-aromatic cyclohexyl ring as defined above and $R^{17}$ and $R^{18}$ are hydrogen; provided that (a.) when G is always —COOR" and (i.) R', R", $R^{14}$ and $R^{16}$ through $R^{20}$ are all hydrogen, then $R^{13}$ and $R^{15}$ are other than hydrogen; (ii.) R" and $R^{13}$ through $R^{20}$ are all hydrogen, and m, n, o, p and q are each 1, then (CR'R') is other than (CH$_2$) and (CHCH$_3$); (iii.) R', R", $R^{13}$, $R^{14}$, $R^{17}$ and $R^{20}$ are all hydrogen, then at least two of $R^{15}$, $R^{16}$, $R^{18}$ and $R^{19}$ are other than methyl; and (iv.) R", $R^{16}$, $R^{19}$ and $R^{20}$ are all hydrogen, and each (CR'R') is independently (CHR') or (CH$_2$CHR'), then $R^{13}$ and $R^{15}$, and $R^{17}$ and $R^{18}$, are other than a fused ring; and (b.) when G is always —P(O)(OR")$_2$, —P(O)(OR")(R") or —C(O)N(R")$_2$, then at least one R' or $R^{13}$ through $R^{20}$ is other than hydrogen;
or a salt or multimeric form thereof.

DETAILED DESCRIPTION OF THE INVENTION

Listed below are definitions of various terms used in the description of this invention. These definitions apply to the terms as they are used throughout this specification, unless otherwise limited in specific instances, either individually or as part of a larger group.

The expression "relaxivity" refers to the effectiveness of a metal chelate to reduce the relaxation time of bulk water in contact with the metal chelate.

The expression "immobilized relaxivity" refers to the relaxivity measured when a chelate moiety can undergo only slow molecular reorientation because of rigid attachment to a large moiety or a physiological surface, or because it is dissolved in a medium of high viscosity.

The expression "water relaxivity" refers to relaxivity in water where a chelate moiety possesses a relaxivity dominated by overall molecular reorientation.

The expression "enhanced relaxivity" refers to relaxivity values made greater than those of well characterized prior art molecules by 1.) altering the electronic relaxation rate, $\tau_s$, through modifications of the metal-donor atom bond vibration frequencies and/or amplitudes, (this being accomplished, for example, by increasing the steric bulk and/or orientation of organic elements bonded to the donor atoms and/or the macrocyclic carbon atoms), 2.) in a multimer by decreasing the internal molecular motion of one monomer unit relative to another (this being accomplished, for example, by increasing the steric bulk of the organic groups linking the monomer units) or 3.) by decreasing the molecular reorientation of a monomer or a multimer attached to a large moiety or a physiological surface.

The term "stability" refers to the equilibrium formation constant (K) of the reaction M+L→M(L) where K=[M(L)]/[M][L], M is a metal ion, L is a chelating ligand and M(L) is a chelate complex of a metal and a ligand.

The term "alkyl" refers to both straight and branched, unsubstituted chains of carbon atoms. Those chains having 1 to 5 carbon atoms are preferred. Methyl is the most preferred alkyl group.

The term "cycloalkyl" refers to cyclic hydrocarbon groups of 3 to 8 carbon atoms. The groups may be unsubstituted or substituted by, for example, alkyl, halogen, hydroxy, hydroxyalkyl, alkoxy, alkanoyl, alkanoyloxy, amino, alkylamino, dialkylamino, alkanoylamino, thiol, alkylthiol, nitro, cyano, carboxy, carbamoyl, alkoxycarbonyl, alkylsulfonyl, sulfonamido and the like.

The term "alkoxy" refers to -alkyl(O). Methoxy is the most preferred alkoxy group.

The term "aryl" refers to phenyl, pyridyl, furanyl, thiophenyl, pyrrolyl, imidazolyl and the like, all of which may be substituted. Preferred substituted aryl groups are those substituted with 1, 2 or 3 halogen, nitroamino, maleimido, isothiocyanato, hydroxy, hydroxyalkyl, alkyl, alkoxy, carbamoyl, carboxamide, acylamino or carboxy moieties.

"Hydroxyalkyl" refers to straight and branched alkyl groups including one or more hydroxy radicals such as —CH$_2$CH$_2$OH, —CH$_2$CH$_2$OHCH$_2$OH, —CH(CH$_2$OH)$_2$ and the like. (See, for example, Sovak, M., Editor, *Radiocontrast Agents*, Springer-Verlag, 1984, pp. 1–125).

The term "aralkyl" refers to an aryl group bonded through an alkyl group.

The term "carbocyclic ring" refers to a ring system in which all the ring atoms are carbon, e.g., phenyl or cyclohexyl. The ring may be unsubstituted or substituted by, for example, alkyl, halogen, hydroxy, hydroxyalkyl, alkoxy, alkanoyl, alkanoyloxy, amino, alkylamino, dialkylamino, alkanoylamino, thiol, alkylthiol, nitro, cyano, carboxy, carbamoyl, alkoxycarbonyl, alkylsulfonyl, sulfonamido and the like.

The term "halogen" refers to bromo, chloro, fluoro or iodo.

The term "alkanoyl" refers to the group alkyl-C(O)—.

The term "alkanoyloxy" refers to the group alkyl-C(O)—O—.

The term "amino" refers to the group —NH$_2$.

The term "alkylamino" refers to the group —NHR where R is alkyl.

The term "dialkylamino" refers to the group —NRR' where R and R' are each, independently, alkyl.

The term "alkanoylamino" refers to the group alkyl-C(O)—NH—.

The term "thiol" refers to the group —SH.

The term "alkylthiol" refers to the group —SR where R is alkyl.

The term "nitro" refers to the group —NO$_2$.

The term "cyano" refers to the group —CN.

The term "carboxy" refers to the group —C(O)OH or the group —C(O)OR where R is alkyl.

The term "alkoxycarbonyl" refers to the group alkoxy-C—(O)—.

The term "alkylsulfonyl" refers to the group alkyl-SO$_2$—.

The term "sulfonamido" refers to the group —SO$_2$NH$_2$, the group —SO$_2$NHR or the group —SO$_2$NRR' where R and R' are each, independently, alkyl, cycloalkyl or aryl.

The term "carbamoyl" refers to the group —C(O)NH$_2$, the group —C(O)NHR or the group —C(O)NRR' where R and R' are each, independently, alkyl, alkoxy or hydroxyalkyl.

The term "carboxamide" refers to the group —C(O)NH$_2$, the group —C(O)NHR or the group —C(O)NRR' where R and R' are each, independently, alkyl.

The term "acylamino" refers to the group —NH—C(O)—R where R is alkyl.

The expressions "bioactive group" and "bioactive moiety" denote a group which is capable of functioning as a metabolic substrate, catalyst or inhibitor, or is capable of being preferentially taken up at a selected site of a subject, such as by possessing an affinity for a cellular recognition site.

When compounds of the formula I are in the multimeric form, each monomer is preferably linked by a cyclic bridging group represented by the general formula II:

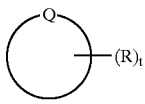

II wherein

Q is a 4- to an 8-membered carbocyclic ring which may be fully or partially saturated;

t is an integer from 2 to 16;

each R group is independently hydrogen, —OH, —CH$_2$—A, —OCH$_2$CH(OH)CH$_2$—A or a functional group capable of forming a conjugate with a biomolecule, provided that at least two of the R groups are selected from —CH$_2$—A or —OCH$_2$CH(OH)CH$_2$—A; and A is the monomer of formula I.

Of course, the cyclic bridging group may be used to link known moieties as well. Where it is a known moiety which is being linked by the cyclic bridging group of formula II, A is any moiety capable of chelating a metal atom.

Preferred bridging groups of the formula II are those wherein

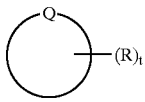

is a compound of the following formula III:

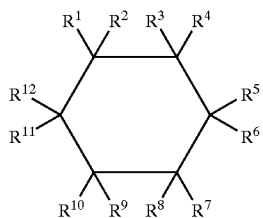

wherein each R$^1$ through R$^{12}$ group is independently hydrogen, —OH, —CH$_2$—A, —OCH$_2$CH(OH)CH$_2$—A or a functional group capable of forming a conjugate with a biomolecule;

at least two of R$^1$ through R$^{12}$ are selected from —CH$_2$—A or —OCH$_2$CH(OH)CH$_2$—A;

R$^8$ and R$^9$ taken together may additionally form the group —O—[C(RR)]—O— where each R is independently hydrogen or alkyl, or R$^8$ and R$^9$ taken together may form

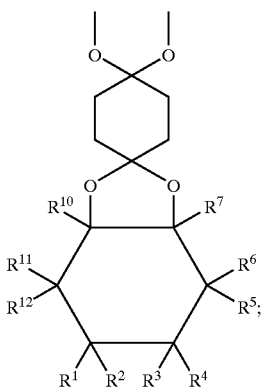

and

A is a moiety described above.

When A is a known monomer, for example, A is preferably

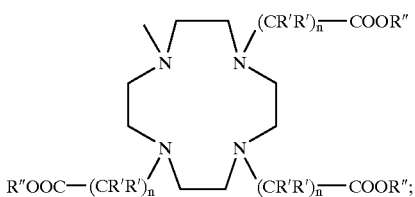

wherein
each R' is independently hydrogen, alkyl, alkoxy, hydroxyalkyl, aryl, aralkyl or arylalkoxy;
each R" is hydrogen; and
each n is 1 or 2;
or a salt thereof.

Contrast agents with significantly enhanced relaxivities are of great interest, not only because they offer improved efficacy at reduced doses for current clinical applications, but also because they may provide the sensitivities needed for imaging various biochemical processes.

Certain preferred compounds having enhanced relaxivities are (i.) chelates possessing a stability greater than or equal to $10^{15}$ M$^{-1}$ and capable of exhibiting an immobilized relaxivity between about 60 and 200 mM$^{-1}$s$^{-1}$/metal atom, for example between about 70 and 150 mM$^{-1}$s$^{-1}$/metal atom, or between about 80 and 100 mM$^{-1}$s$^{-1}$/metal atom; and (ii.) multimeric chelates possessing monomer units with a stability greater than or equal to $10^{15}$ M$^{-1}$, and having relaxivity values (not immobilized) greater than 5 mM$^{-1}$s$^{-1}$/metal atom.

In designing new chelates with these elevated relaxivities, the inventors have noted that immobilized relaxivity can depend strongly, for example, on the structure of the chelate. Without being bound by any particular theory, apparently a mechanism that involves rigidifying the chelate structures in solution with, for example, alkyl substitutions on the tetraaza ring of chelates, especially when the substitution is introduced into the carboxylate arms of the chelates, affects immobilized relaxivity. In the Solomon-Bloembergen-Morgan (SBM) model, the electronic relaxation of a paramagnetic metal complex is viewed as occuring through a dynamic modulation process about the transient zero-field splitting (ZFS) of the metal's electronic spin levels. This transient ZFS is induced by the structural distortion of the metal complex from its ideal symmetry in solution which is thought to be caused by its collision with solvent molecules. Alkyl substitution on either the tetraaza ring or the carboxylate arms of a chelate is thought to reduce the flexibility of the chelate for structural distortion in solution. This in turn reduces the magnitude of ZFS, giving an increased immobilized relaxivity value.

Water relaxivity is generally determined in aqueous Bis Tris buffer (pH 7) solutions by the standard inversion-recovery method (known to those in the art) at 20 MHz and 40° C. (See, e.g., X. Xhang, *Inorganic Chemistry*, 31, 1992, 5597, the entire contents of which are hereby incorporated by reference.) While a mathematical description of the relaxation mechanism at the presence of a paramagnetic species is provided by the classical SBM equations, it is experimentally difficult to explore the dependence of relaxivity on structure because the relaxivity values of most low-molecular weight chelates are often controlled by their rapid tumbling motions in regular aqueous solutions.

To eliminate the overriding effect of molecular tumbling in regular aqueous solutions, the relaxivity of a chelate can be determined in aqueous sucrose solutions or other media that result in a reduction of molecular reorientation of any solute. In these solutions, the relaxivity values approximate, under optimal conditions, the relaxivities of chelates in biologically immobilized systems such as those covalently attached to cell surfaces. Hence, these values in sucrose solutions are defined as immobilized relaxivity. Immobilized relaxivity is generally determined under the same conditions as water relaxivity (see supra) except that the viscosity of the solutions is increased to 80 cp by the addition of solid sucrose to the aqueous solution of chelate, and the temperature is set at 20° C. In the calculation of relaxivity, one uses the concentration of the solute in the aqueous solution (before sucrose is added).

When used for relative comparison, this method serves as a simple screening technique for differentiating chelates designed for efficient biological targeting.

Thus, the compounds of the invention, including compounds of the formula I and formula II, and salts thereof, may be complexed with a paramagnetic metal atom and used as relaxation enhancement agents for magnetic resonance imaging. These agents, when administered to a mammalian host (e.g., a human) distribute in various concentrations to different tissues, and catalyze relaxation of protons (in the tissues) that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times, generally either before and after administration of the agents, or after administration only, and the differences in the images created by the agents, presence in tissues are used in diagnosis. In proton magnetic resonance imaging, paramagnetic metal atoms such as gadolinium(III), and manganese(II), chromium(III) and iron(III) (all are paramagnetic metal atoms with favorable electronic properties) are preferred as metals complexed by the ligands of the invention, including the ligands of formula I and formula II. Gadolinium(III) is the most preferred complexed metal due to the fact that it has the highest paramagnetism, it has low toxicity when complexed to a suitable ligand, and it has high lability of coordinated water. When the distance between the monomeric gadolinium chelate units in a complex is at least about 6 angstroms, the complexes tend to be sufficiently stable. Those compounds of formula II, when complexed with gadolinium(III) ions, are particularly useful. The distance between the monomeric gadolinium chelate units in these complexes is generally greater than 6 angstroms (although in certain circumstances a distance of 4.5 angstroms is sufficient), and the rigid bridges of these complexes assist in reducing independent motion of the gadolinium ions.

The metal-chelating ligands of the present invention can also be complexed with a lanthanide (atomic number 58 to 71) and used as chemical shift or magnetic susceptibility agents in magnetic resonance imaging or in magnetic resonance in vivo spectroscopy.

While the above-described uses for the metal-chelating ligands of the present invention are preferred, those working in the diagnostic arts will appreciate that the ligands can also be complexed with the appropriate metals and used as contrast agents in other imaging techniques such as x-ray imaging, radionuclide imaging and ultrasound imaging, and in radiotherapy.

USE IN IMAGING

To use the ligands of the present invention for imaging, they are first complexed with an appropriate metal. This may be accomplished by methodology known in the art. For example, the metal can be added to water in the form of an oxide or in the form of a halide or acetate and treated with an equimolar amount of a ligand of the present invention. The ligand can be added as an aqueous solution or suspension. Dilute acid or base can be added (where appropriate) to maintain a suitable pH. Heating at temperatures as high as 100° C. for periods of up to 24 hours or more may sometimes be employed to facilitate complexation, depending on the metal and the chelator, and their concentrations.

Pharmaceutically acceptable salts of the metal complexes of the ligands of this invention are also useful as imaging agents. They can be prepared by using a base (e.g., an alkali metal hydroxide, meglumine, arginine or lysine) to neutralize the above-prepared metal complexes while they are still in solution. Some of the metal complexes are formally uncharged and do not need cations as counterions. Such neutral complexes may be preferred in some situations as intravenously administered x-ray and NMR imaging agents over charged complexes because they may provide solutions of greater physiologic tolerance due to their lower osmolality.

The present invention also provides pharmaceutical compositions comprising a compound of the invention, including a compound of the formula I or II, or a salt of one of these compounds, optionally complexed with a metal, and a pharmaceutically acceptable vehicle or diluent. The present invention further provides a method for diagnostic imaging comprising the steps of administering to a host a compound of the invention, or a salt thereof, which is complexed with a metal, and obtaining a diagnostic image, preferably a magnetic resonance image, of said host.

Sterile aqueous solutions of the chelate complexes of the present invention are preferably administered to mammals (e.g., humans) orally, intrathecally and, especially, intravenously in concentrations of about 0.003 to 1.0 molar. The metal complexes of the present invention may be employed for visualization of various sites. For example, for the visualization of brain lesions using magnetic resonance imaging, a gadolinium complex of a ligand of the invention, including a ligand of the formula I or formula II, may be administered intravenously at a dose of 0.001 to 0.5 millimoles of the complex per kilogram of body weight, preferably at a dose of 0.001 to 0.3 millimoles/kilogram. For visualization of the kidneys, the dose is preferably 0.05 to 0.20 millimoles/kilogram. For visualization of the heart, the dose is preferably 0.001 to 0.3 millimoles/kilogram. For visualization of the liver, the dose is preferably 0.001 to 0.3 millimole/kilogram.

The pH of the formulation of the present metal complexes is preferably between about 6.0 and 8.0, most preferably between about 6.5 and 7.5. Physiologically acceptable buffers (e.g., tris(hydroxymethyl)-aminomethane) and other physiologically acceptable additives (e.g., stabilizers such as parabens) may also be present.

It is also advantageous to employ dual scavenging excipients such as those described in copending application U.S. Ser. No. 032,763, filed Mar. 15, 1993, entitled "DUAL FUNCTIONING EXCIPIENT FOR METAL CHELATE CONTRAST AGENTS", incorporated herein by reference. Those excipients have a general formula corresponding to:

$$D_s[D'(L')]_t$$

wherein D and D' are independently Ca or Zn, L' is an organic ligand which may be different from, or the same as, the ligand employed to complex the metal, and s and t are independently 1, 2 or 3.

As already noted, the present invention further includes multimeric forms of the compounds of the invention, including those of formula I and formula II, such as dimers, trimers, tetramers, etc. Known functional groups and technology are readily useable to provide such multimers.

Compounds of the present invention may include those containing functional group(s) capable of forming a conjugate with a biomolecule. These compounds are preferably chelates, including a functional group, capable of exhibiting an immobilized relaxivity between about 60 and 200 $mM^{-1}s^{-1}$/metal atom, for example between about 70 and 150 $mM^{-1}s^{-1}$/metal atom, or between about 80 and 100 $mM^{-1}s^{-1}$/metal atom. Similarly, the chelates, once conjugated to a biomolecule of size greater than or equal to about 40,000 daltons, are also preferably capable of exhibiting a relaxivity between about 60 and 200 $mM^{-1}s^{-1}$/metal atom, for example between about 70 and 150 $mM^{-1}s^{-1}$/metal atom, or between about 80 and 100 $mM^{-1}s^{-1}$/metal atom. Preferred biomolecules are peptides, polypeptides and oligosaccharides or fragments thereof, although other biomolecules such as proteins, particularly monoclonal antibodies, lipids, sugars, alcohols, bile acids, fatty acids, receptor-binding ligands, amino acids and RNA, DNA or modified fragments of these may be conjugated to the compounds of the present invention. For smaller biomolecules, the enhanced relaxivity afforded by the chelates of this invention may be more fully realized when the chelate-biomolecule conjugate becomes immobilized in vivo, such as by binding to a receptor on a cell surface or by binding to another biomolecule.

Conjugates where a compound of the invention, or salt and/or multimer thereof, is linked to a biomolecule such as a protein, provided by the present invention, are novel, as are metal complexes and pharmaceutical compositions containing, and methods of using (e.g., for imaging), the aforementioned conjugates. Conjugation may be achieved in vitro, such as by use of known conjugation methodologies, or in situ in a living subject by administration of a compound containing one or more of the aforementioned functional groups.

For linking the compounds of the present invention to a protein, the R groups may be reacted with a protein to produce a protein conjugate. Preferred proteins are those in serum, wherein the compound of the invention is directly injected and the conjugate is formed in situ. It is understood that other functional groups, as described above, may be used to link the bifunctional metal-chelating ligands of this invention to proteins such as monoclonal antibodies or fragments thereof.

Compounds of the formula I can generally be prepared as follows:

Ligands in which the aza macrocyclic ring carbon atoms are modified are built de novo from suitable aziridine precursors by cyclotetramerization.

Cyclotetramerization of N-benzylaziridine has been reported in the literature. (See, for example, T. E. Burg and G. R. Hansen, *J. Heterocyclic Chemistry*, (1968), 5, 305.) The synthetic approach to the preparation of S,S,S,S-tetramethyltetraazacyclododecane (5) is given in scheme 1:

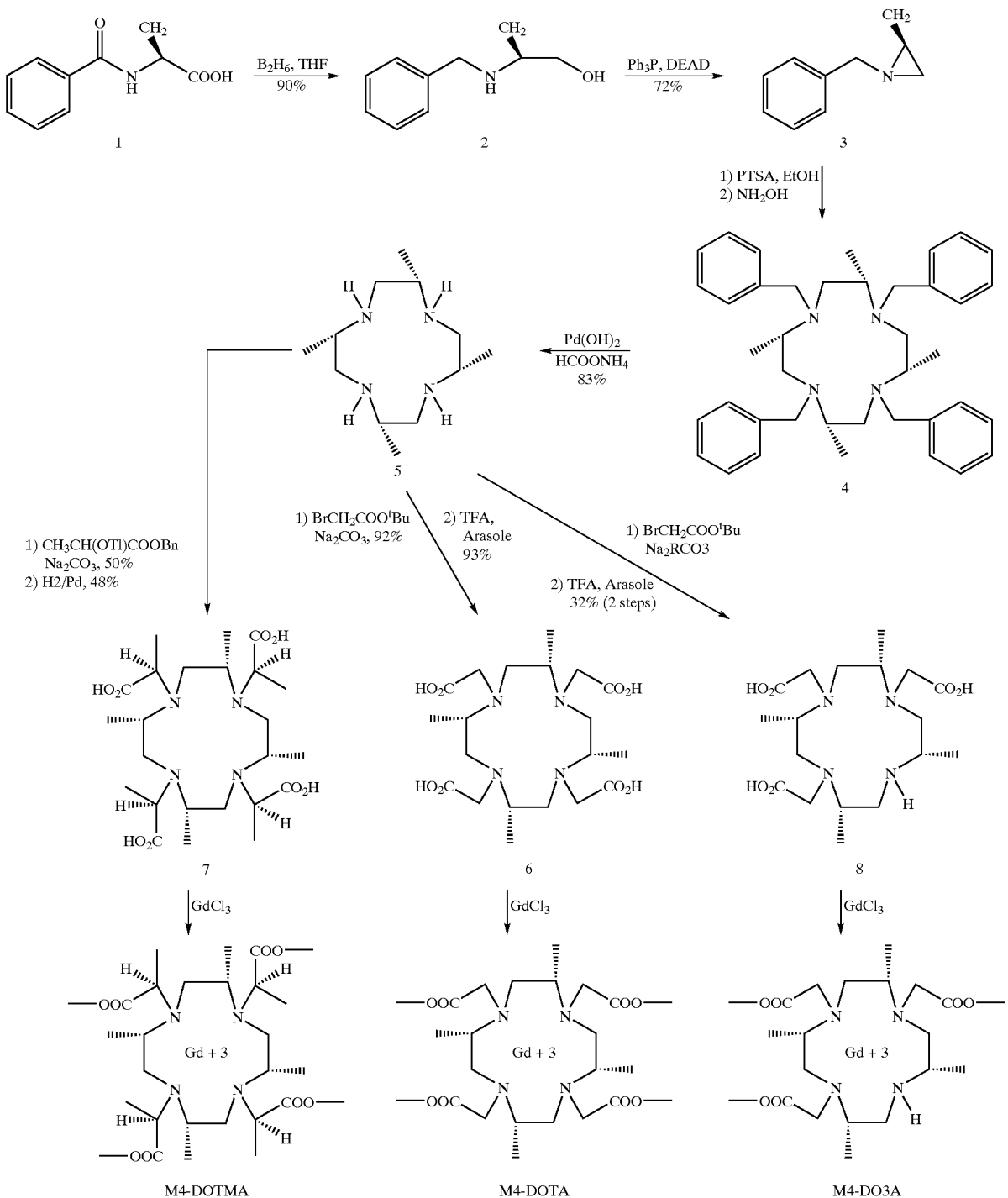

SCHEME 1

[S]-N-Benzoylalanine(1) is reduced with diborane to yield [S]-N-benzylalaninol(2). Under Mitsunobu conditions, compound (2) affords [S]-N-benzyl-2-methyl aziridine(3). Cyclotetramerization under p-toluene sulfonic acid catalysis in ethanol, followed by treatment with ammonium hydroxide ($NH_4OH$), furnishes S,S,S,S-tetra-N-benzyltetramethyltetraazacyclododecane(4), which is debenzylated under transfer hydrogenolytic conditions to obtain S,S,S,S-tetramethyltetraazacyclododecane(5).

Tetraalkylation of compound (5) with t-butyl bromoacetate in the presence of sodium carbonate, followed by deprotection with trifluoroacetic acid and anisole, affords the ligand (6).

Tetraalkylation of compound (5) with benzyl 2-triflyloxylactate (prepared as described by S. I. Kang et al., *Inorg. Chem.*, (1993), 32, 2912–2918) in the presence of sodium carbonate, followed by catalytic hydrogenolytic debenzylation furnishes the ligand (7).

Tris-alkylation of compound (5) with t-butyl bromoacetate in the presence of sodium bicarbonate, followed by deprotection by treatment with trifluoroacetic acid and anisole, provides the ligand (8).

For preparing multimeric ligands, 1,4,7-tris-carboxymethyl-1,4,7,10-tetraazacyclododecane-10-yl (DO3A) units, for example, are attached to a bridging unit by two different methods. In the first method, a spiro epoxide on the bridging unit is used to alkylate DO3A. In the second method, a glycidyloxy moiety is attached to the bridging unit which then is used to alkylate DO3A.

By way of example, N-alkylation of DO3A with suitable epoxides of formula (9) below, wherein X is a carbocyclic, fused heterocyclic or spiro-heterocyclic unit, and n is 2, 4 or 8, affords multimeric ligands of the formula (10):

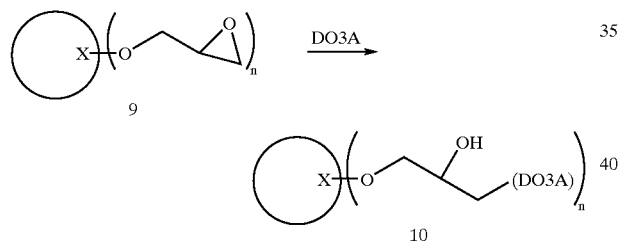

Epoxides of formula (9) are generated by the Prilezhaev Reaction in which olefins of formula (11) are treated with peracids such as m-chloroperbenzoic acid:

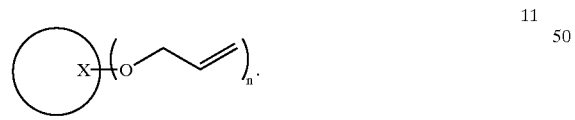

Olefins of formula (11) are generated by the alkylation of alcohols of formula (12):

Another mode of attachment of DO3A would be to epoxidize olefins of formula (13) to obtain epoxides of formula (14), and then alkylating DO3A with the epoxides to form ligands of formula (15):

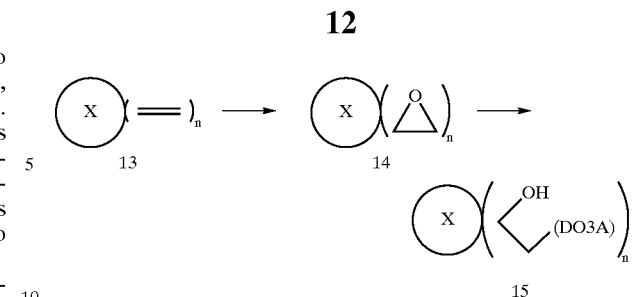

These two method of attachment of DO3A could also be present in the same bridging unit X leading to structures as in formula (16):

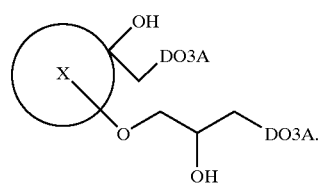

Representative bridging units are exemplified in formulas (17), (18), (19), (20), (21) and (22):

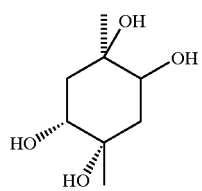

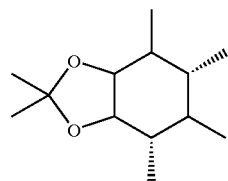

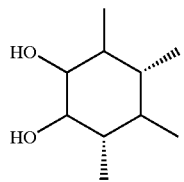

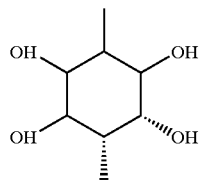

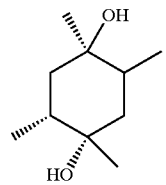

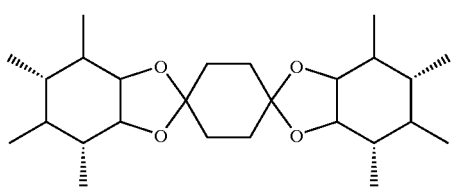

22

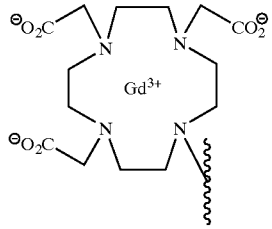

The structures shown in formulas (17) to (22) are only by way of representative examples. They will, in actuality, be a mixture of all the possible diastereomers, if the attachment is through a 2-hydroxypropyloxy link. In the case of formula 22, for example, in addition to the presence of diastereomers, the product would also consist of the various geometric isomers that could result when the two myo-inositol molecules are coupled to each other. The coupling of the two myo-inositol units is achieved by reacting the compound of formula (23) with cyclohexane-1,4-dione (24):

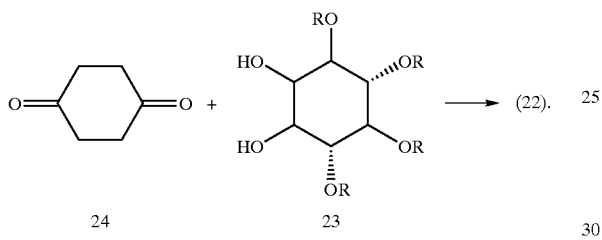

The bridging unit for formula 17 is generated from commercially available diethyl cyclohexane-1,4-dione-2,5-dicarboxylate by lithium aluminum hydride reduction as described in J. G. Murphy, *J. Med. Chem.*, (1966), 9, 157.

The bridging unit for formula (18) is generated by treating myo-inositol (25) with 2,2-dimethoxypropane in the presence of p-toluene sulfonic acid as descirbed by Giggs et al., *Carbohydrate Res.*, 1985, 1, 132:

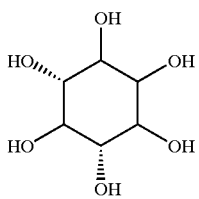

25

The bridging unit (19) is made from (18) by acidic hydrolysis. The unit (20) is prepared from myo-inositol (25) by reaction with excess 2,2-dimethoxypropane in the presence of p-toluenesulfonic acid. The unit (21) is made from the bis-epoxide precursor to the unit (17) by methods desribed above for functionalizing hydroxy groups.

The ligand of Example (10), below, bearing a phosphonomethyl arm, is made by treating DO3A with phosphorus acid and formaldehyde as described by M. Tazaki et al., *Chem. Lett.*, 1982, 571.

All stereoisomers of the compounds and complexes of the present invention are contemplated herein, whether alone (that is substantially free of other isomers), in a mixture of certain stereoisomers (for example, as a racemate) or in any other mixture thereof.

The invention will now be further described by the following examples. In the structures of examples 1–6, R is

EXAMPLE 1

(1α,2α,4β,5β)-10,10'-[(1,2,4,5-Tetrahydroxy-1,4-cyclohexanediyl)bis(methylene)]bis[1,4,7,10-tetraazacyclododecane-1,4,7-triacetic Acid], Digadolinium Salt

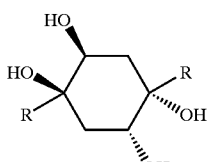

A. trans-2,5-Dihydroxy-1,4-dimethylene Cyclohexane

A warm solution of dry, recrystallized diethyl 1,4-cyclohexanedione-2,5-dicarboxylate (30.75 g, 120 mmol) in 350 ml anhydrous tetrahydrofuran (THF) was added to a refluxing solution of 1.0 M LAH in THF (600 mL) over a 2 hour period. After an additional 1.5 hours at reflux and subsequent cooling, a saturated solution of aqueous Rochelles's salt (app. 73 mL) was added dropwise to the reaction mixture. The tartrate complex was filtered, washed with THF and the filtrate was concentrated to a paste. The paste was recrystallized from hot ethyl acetate; yield 4.39 g (31.3 mmol, 26.1%). A second recrystallization yielded 3.81 g (27.2 mmol, 22.6%).

M.P.: 160–161.5° C., uncorrected (lit. 162.5–163° C.).

B. (3α,4α,6β,9β)-1,7-Dioxadispiro[2.2.2.2]-decane-4,9-diol

A solution of wet, 80% m-chloroperoxybenzoic acid (mCPBA, 7.00 g, app. 30 mmol) in 30 mL dry dichloromethane ($CH_2Cl_2$) was dried over anhydrous magnesium sulfate ($MgSO_4$). This solution was added to a solution of dry Compound A (1.40 g, 10.0 mmol) in 15 mL dry $CH_2Cl_2$). The mixture was stirred at room temperature under a dry nitrogen atmosphere for 16 hours. A second sample (550 mg) of mCPBA was added to ensure complete conversion of the dimethylene compound to the diepoxide. After 3 hours, the mixture was evaporated to dryness and excess mCPBA/m-chlorobenzoic acid was removed by treating the residue with diethyl ether. The ether-insoluble material was filtered, washed with ethyl ether ($Et_2O$) and air dried to yield 1.35 g of crude Compound B. The crude material was recrystallized from a minimum of hot methanol; yield 967 mg (5.6 mmol, 56.1%).

M.P.: 231–233° C.

C. (1α,2α,4β,5β)-10,10'-[(1,2,4,5-Tetrahydroxy-1,4-cyclohexanediyl)bis(methylene)]bis[1,4,7,10-tetraazacyclododecane-1,4,7-triacetic Acid], Hexasodium Salt The pH of a suspension of 1,4,7,10-tetra-azacyclododecane-1,4,7-triacetic acid (DO3A)-$H_2SO_4$ (prepared as described in D. D. Dischino et al., *Inorg. Chem.*, 1991, 30, 1265–69; 2.67 g, 6.0 mmol) in 2.0 mL water was adjusted to approximately pH 12.5 with 5.40 mL 5N sodium hydroxide. This solution was warmed to 50° C., and Compound B (517 mg, 3.0 mmol) was added portionwise over 5.5 hours. Crystals developed overnight from the warm mixture. After cooling, the crude crystals (3.4 g) were isolated and were recrystallized from 20 mL hot water to yield 1.3 g (1.4 mmol, 45%) of Compound C.

Mass Spectrum (FAB): (M−7H+8Na)⁺ at 1040; (M−6H+7Na)⁺ at 1019; (M−5H+6Na)⁺ at 997; (M−4H+5Na)⁺ at 975; (M−3H+4Na)⁺ at 953; (M−2H+3Na)⁺ at 931. Elemental analysis: Found: C, 42.53, H, 6.10, N, 10.90. Calculated for: $C_{36}H_{58}N_8Na_6O_{16}\cdot1.16H_2O$: C, 42.49, H, 5.97, N, 11.01.

D. (1α,2α,4β,5β)-10,10'-[1,2,4,5-Tetrahydroxy-1,4-cyclcohexanediyl)bis(methylene)]bis[1,4,7,10-tetraazacyclododecane-1,4,7-triacetic Acid], Digadolinium Salt The pH of a solution of Compound C (760 mg, 762 µmol) in 5.0 mL deionized water was adjusted to pH 4.83 with 225 µL acetic acid (HOAc). A solution of $Gd(OAc)_3\cdot4H_2O$ (680 mg, 1.67 mmol) in 5.0 mL warm deionized water was added to the ligand solution over a 10 minute period; final pH 4.73. After 1 minute of stirring at room temperature, a precipitate began to develop. The volume of the precipitate increased with time and the reaction was left to run overnight. The precipitate was filtered, extensively washed with water, and dried; yield 741 mg (631 µmol, 83%). An analytical sample was prepared by recrystallization from hot water.

Mass spectrum: (FAB): (M+H)⁺ at 1169 through 1177. Elemental analysis: Found: C, 35.93, H, 5.50, N, 8.84. Calculated for $C_{36}H_{58}Gd_2N_8O_{16}\cdot2.5H_2O$: C, 35.49, H, 5.21, N, 9.20.

EXAMPLE 2

(3aα,4α,5β,6α,7β,7aα)-10,10',10'',10'''-[[Hexahydro-2,2-dimethyl-1,3-benzodioxol-4,5,6,7-tetrayl]tetra(oxy)-tetra(2-hydroxy-3,1-propanediyl)] tetrakis[1,4,7,10-tetraazacyclododecane-1,4,7-triacetic Acid], Tetragadolinium Salt

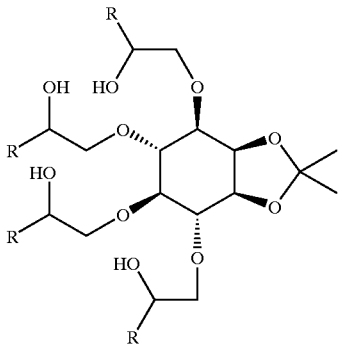

A. (+)-1,2-O-Isopropylidene-myo-inositol

A mixture of myo-inositol (25.0 g, 140 mmol), 2,2-dimethoxypropane (42.5 mL, 350 mmol) and p-toluenesulfonic acid (250 mg) in dimethylsulfoxide (80 mL) was stirred at 100° C. for 45 minutes until the solution became homogenous. After stirring the mixture at ambient temperature for 30 minutes, triethylamine (2.5 mL), ethanol (100 mL) and ether (500 mL) were introduced causing precipitation. The solid material was filtered, washed with ether-methanol (200 mL, 5:1) and ether, and dried to obtain the ketal compound A (9.72 g) as a white solid in 32% yield.

m.p.: 182.4–182.9° C.

B. (3aα,4α,5β,6α,7aα,)-Hexahydro-2,2-dimethyl-tetra-kis-4,5,6,7-(2-propenyloxy)-1,3-benzodioxole To a suspension of sodium hydride (545 mmol) in dimethylformamide (50 mL) was added the ketal compound A (20.0 g, 90.8 mmol) dimethylformamide (20 mL) at ambient temperature under nitrogen. After stirring the suspension for 2 hours, allyl bromide (83.4 g, 689 mmol) in dimethylformamide (50 mL) was reacted for 18 hours. The unreacted sodium hydride was carefully quenched with water, and then the solvent was removed to obtain a dark brown oil. The residue was partitioned in water (100 mL) and dichloromethane (100 mL) and extracted with dichloromethane (100 mL×3). The combined organic layers were dried over sodium bisulfate and evaporated to obtain a brownish liquid (about 45 mL). The crude product was purified by silica gel flash chromatography (ethyl acetate and hexanes, 1:8) to afford compound B (26.2 g) as a pale yellow liquid in 76% yield.

C. (3aα,4α,5β,6α,7aα,)-Hexahydro-2,2-dimethyl-tetra-kis-4,5,6,7-(oxiranylmethoxy)-1,3-benzodioxole To compound B (6.0 g, 15.8 mmol) in dichloromethane (10 mL) was added dropwise m-chloroperbenzoic acid (85% from ICN, 19.2 g, 94.6 mmol) dissolved in dichloromethane (100 mL). A homogeneous solution was initially obtained but a white solid, presumed to be m-chlorobenzoic acid, slowly precipitated out of the solution after about 15 minutes. After 24 hours, sodium metabisulfite (100 mL, 5% in water) and sodium bicarbonate (200 mL, 10% in water) were added and the resulting solution was extracted with dichloromethane (100 mL×3). The organic layers were combined and dried over sodium sulfate. The residue, obtained from removal of the solvent, was purified by flash silica gel chromatography to obtain compound C as a colorless liquid in 76% yield.

D. (3aα,4α,5β,6α,7β,7aα,)-10,10',10'',10'''-[[Hexahydro-2,2-dimethyl-1,3-benzodioxol-4,5,6,7-tetrayl]-tetra(oxy)tetra(2-hydroxy-3,1-propanediyl)]tetrakis[1,4,7,10-tetraazacyclododecane-1,4,7-triacetic Acid], Triethylamine (1:4) Salt To a suspension of DO3A (9.77 g, 28.2 mmol) dissolved in alkaline water (6 mL, 10 N sodium hydroxide was used to obtain a pH 10 solution) at 40–50° C. was added the tetraepoxide compound C (1.54 g, 3.46 mmol) in acetonitrile (5 mL). The reaction mixture was stirred for 2 days maintaining the same pH. The crude product was purified by DEAE Sephadex chromatography using triethylammonium bicarbonate (pH 7.5) as the eluent. The buffer concentration to bring out the product compound D was 200 to 500 mM. Removal of the buffer gave compound D (7.8 g) in 58% yield.

m.p.: 178° C. (decomp.).

E. (3aα,4α,5β,6α,7β,7aα)-10,10',10'',10'''-[[Hexahydro-2,2-dimethyl-1,3-benzodioxol-4,5,6,7-tetrayl]tetra(oxy)tetra(2-hydroxy-3,1-propanediyl)]tetrakis[1,4,7,10-tetraazacyclododecane-1,4,7-triacetic Acid], Tetragadolinium Salt To compound D (216 mg, 96 µmol) dissolved in water (1 mL) was added gadolinium acetate (236 mg, 580 µmol) dissolved in water (2 mL). The solution was heated to 65° C. for 18 hours. The pH was maintained between 4.0 and 6.0 during the chelation reaction. The material was loaded to a CHP20P column and eluted with water (1.9 L) followed by 10% ethanolic water (1 L). The product was eluted with 10% ethanol-containing fraction, as identified by HPLC, and evaporated to dryness to yield the title compound (283 mg) as a white crystalline solid in a quantitative yield.

MS (FAB): m/z: 2447.8 [(M+H)⁺, base peak]. Analysis Calculated for $C_{77}H_{124}N_{16}O_{34}Gd_4\cdot11.41H_2O$: C, 34.87; H, 5.58; N, 8.45. Found: C, 34.68; H, 5.98; N, 8.30; H$_2$O, 7.75 (desorprtion KF).

EXAMPLE 3

3,4,5,6-Tetra-O-[2-hydroxy-3-[4,7,10-tris (carboxymethyl)-1,4,7,10-tetraazacyclododecan-1-yl]propyl]-myo-inositol, Tetragadolinium Salt

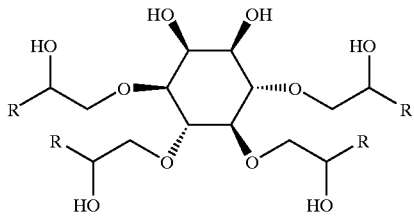

A. 3,4,5,6-Tetra-O-[2-hydroxy-3-[4,7,10-tris-(carboxymethyl)-1,4,7,10-tetraazacyclo-dodecan-1-yl]propyl]-myo-inositol, Tetratriethyl Ammonium Salt Compound D from Example 2 was treated with 1.0 N aqueous hydrochloric acid (10 mL) for 0.5 hours to remove the ketal group. The resulting solution was applied to a polyvinylpyridine (PVP) column (2.5×30 cm) and eluted with water. Silver nitrate was given to test each fraction to detect any breakage of chloride ion. Removal of the water from the fractions containing the product gave the title compound (910 mg) in 80% yield.

m.p.: 210° C. (decomp). MS (FAB): m/z: 1789.9 [(M+H)$^+$, base peak]; 1811.9 [(M+Na)$^+$]. Analysis Calculated for C$_{74}$H$_{132}$N$_{16}$O$_{34}$·11.0H$_2$O: C, 44.63; H, 7.81; N, 11.27. Found: C, 44.63; H, 7.84; N, 11.41; H$_2$O, 6.43 (desorption KF); ROI, 0.17.

B. 3,4,5,6-Tetra-O-[2-hydroxy-3-[4,7,10-tris (carboxymethyl)-1,4,7,10-tetraazacyclo-dodecan-1-yl]propyl]-myo-inositol, Tetragadolinium Salt To gadolinium acetate (595 mg, 1.46 mmol) dissolved in water (1.5 mL) was added Compound A (550 mg, 0.246 mmol) dissolved in water (2 mL). The chelation mixture was kept overnight at 60° C. and the pH of the solution maintained between 4.0 and 5.0. The resulting mixture was loaded to a CHP20P column (2.5×25 cm) and eluted with water followed by 10% ethanol. The title compound was brought out by 10% ethanolic water. Removal of the solvents from the fractions containing the product gave the title compound as a white solid in 93% yield.

MS (FAB): 2408.7 [(M+H)$^+$, $^{158}$Gd)]: Analysis Calculated for C$_{74}$H$_{120}$N$_{16}$O$_{34}$Gd$_4$·4.86H$_2$O: C, 35.63; H, 5.24; N, 8.98. Found: C, 35.48; H, 5.74; N, 8.75; 3.51 H$_2$O (desorption KF); ROI, 31.52.

EXAMPLE 4

(1α,2α,3α,4β,5α,6β)-10,10'-[(2,3,5,6-Tetrahydroxy-1,4-cyclohexanediyl)bis(2-hydroxy-3,1-propanediyl)]-bis[1,4,7-10-tetraazacyclododecane-1,4,7-triacetic Acid], Digadolinium Salt

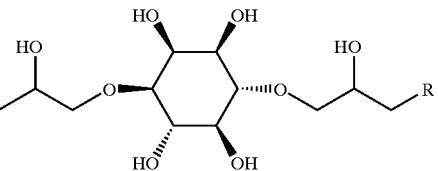

A. [3aR-(3aα,4α,4aα,7aα,8β,8b)]-Hexahydro-2,2,6,6-tetramethyl-4,8-bis-(2-propenyl-oxy)benzo[1,2-d:4.5-d']bis[1,3]dioxole A sample of sodium hydride (NaH) (8.31 g, 156 mmol; 45% in mineral oil) was added to an ice cold solution of dry 1,2:4,5-di-O-isopropylidene-myo-inositol (10.00 g, 38.4 mmol, prepared as indicated in Gigg et al., Carbohyd. Res., 1985, 142, 132) in dry dimethylformamide (DMF) (80 ml). After stirring for 0.5 hours at room temperature, allyl bromide (8.31 mL, 96 mmol) was added dropwise over 5 minutes. During the addition, the temperature was maintained at 25° C. by cooling in a cold water bath. After 1.5 hours, the reaction was stopped by the careful addition of water and the mixture was evaporated to dryness in vacuo. The residue was dissolved in water, extracted with ethyl acetate (EtOAc) (4×50 ml), and washed with water (2×20 ml) and brine (1×20 ml). The organic layer was dried over sodium sulfate (Na$_2$SO$_4$) and evaporated to dryness under reduced pressure. The residue was recrystallized from hexane to give pure product as a colorless solid (12.88 g, yield 98.5%).

M.P. 82–83° C., uncorrected.

B. (3aα,4α,4aα,7aα,8β,8b)-Hexahydro-2,2,6,6-tetramethyl-4,8-bis(oxiranylmethoxy)benzo[1,2-d:4,5-d']bis[1,3]dioxole A solution of 80% mCPBA (13.09 g, 60.7 mmol) in dry dichloromethane (CH$_2$Cl$_2$) (95 ml) was added to a cooled solution containing Compound A (5.11 g, 15.0 mmol) in dry CH$_2$Cl$_2$ (15 ml). After stirring at room temperature overnight, the mixture was treated with saturated aqueous sodium sulfite (Na$_2$SO$_3$) followed by saturated aqueous sodium bicarbonate (NaHCO$_3$) until the aqueous layer was neutral. The organic layer was dried over sodium sulfate (Na$_2$SO$_4$) followed by evaporation to dryness in vacuo. The residue was recrystallized from hot ethanol to give the pure product (4.05 g, yield 72.4%).

M.P. 103–105° C. (uncorrected).

C. (1α,2α,3α,4β,5α,6β)-10,10'-[(2,3,5,6-Tetrahydroxy-1,4-cyclohexanediyl)bis(2-hydroxy-3,1-propanediyl)]bis[1,4,7-10-tetraazacyclododecane-1,4,7-triacetic Acid], Triethylamine (1:2) Salt A sample of crude (3aα,5α,5β,6α,7β,7aα)-10-10'-[[hexahydro-2,2-dimethylbenzol[1,2-d:4,5-d']-bis[1,3]dioxol-4,8-diyl]di(oxy)di(2-hydroxy-3,1-propanediyl)]bis[1,4,7,10-tetraazacyclododecane-1,4,7-triacetic acid] was prepared by heating a solution of DO3A.H$_2$SO$_4$ (28.24 g, 63.5 mmol) and Compound B (5.92 g, 15.9 mmol) in 10 M sodium hydroxide (NaOH) (28.0 mL), H$_2$O (20 mL) and 1,4-dioxane (17 mL) at 50° C. for 70 hours. The pH of the crude mixture was adjusted to pH 1 using 1N hydrochloric acid (HCl) and was heated at 55° C. for 1.5 hours. After the hydrolysis was complete, the pH of the solution was adjusted to 9 with dilute NaOH and the mixture was applied to a DEAE-Sephadex A-25 column ($HCO_3^-$ form, 2L). The column was washed with water, and the product was eluted with a linear gradient of 5–250 mM TEAB buffer (pH 7.5, 4 L each). The fractions which contained pure Compound C were combined, freed of TEAB, and lyophilized to give Compound C as the di(triethylammonium) salt (18.22 g, yield 97.2%). The mass spectral analysis of this product indicated the presence of chloride ion. A sample of the contaminated product (10.00 g) was dissolved in water and was applied onto a AG50W×8 column ($H^+$ form, 500 ml). The column was washed with water, and the product was eluted with 0.5 M ammonium hydroxide ($NH_4OH$). The fractions which contained Compound C were combined and evaporated to give the ammonium salt (2.91 g). The ammonium salt was dissolved in water, applied to a DEAE-Sephadex A-25 column ($HCO_3^-$ form, 2L). The column was washed with water and the product was eluted with 200 mM TEAB (pH 7.5, 5L). The fractions containing pure material were combined, freed of TEAB, and lyophilized to give pure Compound C as the di(triethylammonium) salt (2.86 g, theo. yeild 25.9%).

D. (1α,2α,3α,4β,5α,6β)-10,10'-[(2,3,5,6-Tetrahydroxy-1,4-cyclohexanediyl)]bis(2-hydroxy-3,1-propanediyl)]bis[1,4,7,10-tetraazacyclododecane-1,4,7-triacetic Acid], Digadolinium Salt A sample of Compound C (1.02 g) was dissolved in a solution containing $Gd(OAc)_3.4H_2O$ (1.219 g, 3 mmol) in water (10 mL) and was heated at 50° C. for 16 hours. The solution was applied onto a CHP20-P column (500 mL). The salt contaminants were eluted with water, and the product was eluted with 10% ethanol in water. The appropriate fractions were combined and evaporated to dryness in vacuo. The glassy residue was dissolved in water, and lyophilized to give pure title compound (1.04 g, yield 80.5%).

MS (FAB): $(M+H)^+$ at 1295.2 (major isotope). Elemental analysis: Found: C, 36.83; H, 5.63; N, 8.46%. Calculated for $C_{40}H_{66}Gd_2N_8O_{20}.1.20H_2O$: C, 36.53; H, 5.24; N, 8.52%.

EXAMPLE 5

10-[[1,4-Dihydroxy-2,5-bis[2-hydroxy-3-[4,7,10-tris-(carboxymethyl)-1,4,7,10-tetraazacyclododecan-1-yl]-propoxy]-4-[[4,7,10-tris(carboxymethyl)-1,4,7,10-tetraazacyclododecan-1-yl]methyl]cyclohexyl]methyl]-1,4,7,10-tetraazacyclododecane-1,4,7-triacetic Acid, Tetragadolinium Salt

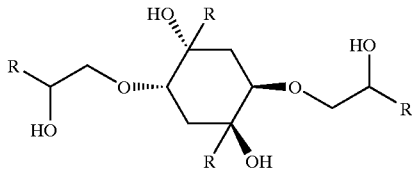

A. 1,7-Dioxadispiro[2,2,2,2]-decane-4,9-diallyldiol

To a suspension of sodium hydride (432 mg, 18 mmol) in anhydrous dimethylformamide (15 ml), a solution of bisepoxydiol (1.0 g, 6 mmol) (described in Example 1B) in anhydrous dimethylformamide (60 ml) was added dropwise and the mixture was stirred at room temperature for 60 minutes. Allyl bromide (2.178 g, 18 mmol) was added and the mixture was stirred at room temperature for 18 hours. Excess of sodium hydride was decomposed with water (2 ml), dimethylformamide removed in vacuo and the residue extracted with ethyl acetate (2×100 ml), washed with water (2×50 ml) and dried. Solvent removal afforded the crude product. Silica gel (25 g) column chromatography using hexanes and ethyl acetate (2/1) as the eluent afforded the pure diallyl derivative compound A as a colorless solid (0.7 g, yield 48%).

Melting point: 63.5–65.5° C. (uncorrected).

B. (3α,4α,6β,9β)-4,9-bis(Oxiranylmethoxy)-1,7-dioxadispiro[2.2.2.2]decane

A solution of m-chloroperoxybenzoic acid (4.3 g, 80%, 18.5 mmol) in dichloromethane (30 ml) was dried over anhydrous magnesium sulfate. This solution was added dropwise to a solution of compound A (1.25 g, 5 mmol) in dry dichloromethane (25 ml). The reaction mixture was stirred at room temperature for 20 hours. Excess of m-chloroperoxybenzoic acid was decomposed with saturated aqueous sodium metabisulfate solution (15 ml). The organic layer was separated, washed with saturated sodium bicarbonate (2×50 ml), and with water (2×50 ml). The organic layer was dried over magnesium sulfate and evaporated to dryness. Recrystallization of the crude material from hot ether afforded the pure tetraepoxide compound B as white crystals (1.1 g, yield 77.5%).

Melting point: 93.0–96.0° C. (uncorrected).

C. 10-[[1,4-Dihydroxy-2,5-bis[2-hydroxy-3-[4,7,10-tris-(carboxymethyl)-1,4,7-10-tetraazacyclododecan-1-yl]-propoxyl-4-[[4,7,10-tris(carboxymethyl)-1,4,7,10-tetraazacyclododecan-1-yl]methyl]cyclohexyl]methyl]-1,4,7,10-tetraazacyclododecane-1,4,7-triacetic Acid, Triethylamine (1:4) Salt A solution of DO3A (17.3 g, 50 mmol) in water was made (80 ml) and the pH of the solution adjusted to 12 with 5 N sodium hydroxide solution. The solution was heated to 80° C. and a solution of compound B (1.42 g, 5 mmol) in dioxane (10 ml) was added dropwise. The mixture was stirred at this temperature for 82 hours. At the end of 82 hours, the pH of the reaction mixture was adjusted to 7 with acetic acid. The mixture was diluted and loaded on to a Sephadex G-25 column. The column was eluted first with 100–250 mM triethyl ammonium bicarbonate (TEAB) buffer and then with 250–500 mM TEAB buffer. Fractions containing the pure tetrameric material were combined and solvent removal afforded the pure product as the tetra triethyl ammonium salt of the title compound as a colorless glassy solid (2.85 g, yield 35%).

Mass Spectrum: 1670 $(M+H)^+$. 102 $(CH_3CH_2)_3N^+H$ Elemental Analysis: Found: C, 53.70; H, 9.15; N, 13.62; $H_2O$, 0.58%. Calculated for $C_{94}H_{184}N_{20}O_{30}.0.67H_2O$: C, 54.11; H, 8.85; N, 13.42; O, 23.52%.

D. 10-[[1,4-Dihydroxy-2,5-bis[2-hydroxy-3-[4,7,10-tris-(carboxymethyl)-1,4,7,10-tetraazacyclododecan-1-yl]-propoxy]-4-[[4,7,10-tris(carboxymethyl)-1,4,7,10-tetraazacyclododecan-1-yl]methyl]cyclohexyl]methyl]-1,4,7,10-tetraazacyclododecane-1,4,7-triacetic Acid, Tetragadolinium Salt A sample of Compound C (0.2 g) was dissolved in 3 mL deinonized water (reactant I). In a separate vial, 0.18 g of $GdCl_3$ powder was dissolved in 5 mL deionized water (reactant II). At about 70° C. and constant stirring, reactant I was added into reactant II dropwise over a time period of several hours. Meanwhile, 5N NaOH was pipetted into the solution from time to time to neutralize the protons released from chelation and maintain the reaction pH around 6. The excess metal ions were precipitated in the form of $M(OH)_3.xH_2O$ by raising solution pH to about 9 and incubating at both about 70° C. and room temperature for several hours. The precipitate was subsequently removed through centrifugation and filtration with 0.22 μm membrane. The filtrate was finally condensed and neutralized to pH 7 in preparation for HPLC purification.

The crude chelate product was purified by preparative HPLC, using mobile phase gradient (acetonitrile:water) and silica-based reverse phase column (YMC C18, 5μ, 200 A). The solvent was removed from the fractions containing the product. The residue was further dried in a vacuum oven at about 70° C. overnight. The yield of the desired chelate was 70%.

Mass Spectrum (FAB, m/e): $(Gd^{159}+H)^+$ at 2287.5. Elemental Analysis (C, H, N): Calculated for $C_{70}H_{112}N_{16}O_{30}Gd_4 \cdot 7.73H_2O$: C, 34.66, H, 5.30, N, 9.24%. Found: C, 34.26, H, 5.36, N, 9.08%.

EXAMPLE 6

[3aR-(3aα,3"aα,4β,4"β,5α,5"α,6β,6"b,7α,7"α,7aα, 7"aα)]-Dodecahydro-4,4",5,5",6,6",7,7"-octakis-[[2-hydroxy-3-[(4,7,10-tricarboxymethyl)-1,4,7,10-tetraazacyclododecan-1-yl]propyl]-oxy]dispiro-[1,3-benzodioxole-2,1'-cyclo-hexane-4',2"-1,3]-benzodioxole], Octagadolinium Salt

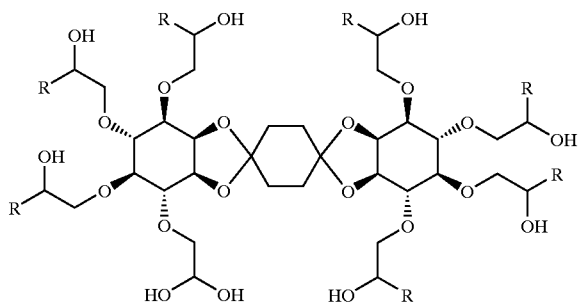

A. (+)-3,4,5,6-Tetra-O-allyl-myo-inositol

Compound B from Example 2 (15.3 g, 44.9 mmol) was dissolved in methanol (30 mL) and treated with 3N hydrochloric acid (30 mL), with constant stirring at room temperature for 13 hours. The reaction mixture was neutralized with saturated sodium bicarbonate solution and extracted with methylene chloride (50 mL×3). The dichloromethane layers were combined and dried with sodium sulfate, filtered, evaporated in vacuo and purified by column chromatography (silicon dioxide, ethyl acetate: hexanes (1:1 v/v)) to obtain 9.1 g (67%) of the desired product compound A.

B. [3aR-(3aα,3"aα,4α,4"β,5β,5"α,6α,6"β,7β,7"α,7aα, 7"aα)]-Dodecahydro-4,4",5,5",6,6",7,7"-octakis-(2-propenyloxy)-dispiro[1,3-benzo-dioxole-2,1'-cyclohexane-4',2"-[1,3]-benzodioxole]

A mixture of the diol compound A (1.0 g, 2.94 mmol), 1,4-cyclohexanedione (165 mg, 1.47 mmol) and p-toluenesulfonic acid (55 mg, 0.289 mmol) was heated in toluene (30 mL) at reflux for 19 hours. The crude reaction mixture was purified by flash silica gel column chromatography (about 200 g) using different eluents of hexane and ethyl acetate (2:1, 1:1 and 1:2, 500 mL each). Three to four spots that have the molecular ion peak at 757 (m/z) were pooled to afford an oil (520 mG) in 43% yield, and the resulting mixture used as a mixture of the isomers of the expected octa-allyl bis-ketal product.

TLC: $R_f$ 0.45, 0.37 and 0.32 in hexanes and: acetone (5:1, v/v).

C. [3aR-(3aα,3"aα,4β,4"β,5α,5"α,6β,6"b,7α,7"α,7aα, 7"aα)]-Dodecahydro-4,4",5,5",6,6",7,7"-octakis-(oxyranylmethoxy)-dispiro[1,3-benzodioxole-2,1'-cyclohexane-4',2"-[1,3]-benzodioxole]

The oxidation of the octa-allyl compound B (1.13 g, 1.49 mmole) by m-chloroperoxybenzoic acid (3.0 g, 85%, 17.6 mmole) in dichloromethane (20 mL) was carried out at ambient temperature for 50 hours. The white solid, which precipitated out, during the oxidation was identified as m-chlorobenzoic acid by $^1$H-NMR (CDCl$_3$). After removal of the solid by filtration, the dichloromethane filtrate was treated with sodium metabisulfite and sodium hydroxide where the final pH of the aqueous layer was 11.7. The organic layer was dried over sodium sulfate and concentrated in vacuo. The crude solid product was purified by column chromatography (flash silica gel, 75 g) to obtain a white solid (670 mg) in 51% yield.

D. [3aR-(3aα,3"aα,4β,4"β,5α,5"α,6β,6"b,7α,7"α,7aα, 7"aα)]-Dodecahydro-4,4", 5,5",6,6",7,7"-octakis-[[2-hydroxy-3-[(4,7,10-tricarboxymethyl)-1,4,7,10-tetraazacyclo-dodecan-1-yl]propyl]oxy]dispiro-[1,3-benzodioxole-2,1'-cyclohexane-4',2"-[1,3]-benzodioxole]

The octaepoxide Compound C (200 mg, 235 μmol) in acetonitrile (0.5 mL) was added to DO3A (2.41 g, 7.04 mmol) in water (4–5 mL) whose pH was adjusted to 9.6 by 10 N sodium hydroxide at 60° C. The resulting solution was kept for 48 hours and analyzed by PRP-X 100 HPLC column at desirable intervals. Two relatively pure fractions were obtained after two DEAE Sephadex A-25 ion exchange columns. One eluted by 300–400 mM triethyl-ammonium bicarbonate (TEAB) showed a peak at m/z 3328.0 corresponding to the heptamer, whereas the other by 400 mM TEAB turned out to be the expected octamer with a peak at m/z 3656.6 ($C_{154}H_{268}N_{32}O_{68}$).

$^1$H-NMR (D$_2$O): d 1.15 (t, 106H, CH$_3$CH$_2$N); 1.7–1.9 (m, methylenes of the middle cyclohexane, 8H); 3.07 (q, 71H, CH$_3$CH$_2$N), 2.8–4.6 (m, 228H, all of methines and methylenes of the octamer ligand except the triethylamine and bridged cyclohexane). $^{13}$C-NMR (D$_2$O): 8.10 and 46.29 (CH$_3$CH$_2$N of triethyl-amine); 41.88, 46.29, 49.25, 49.54, 49.62, 49.76, 50.04, 55.72, 56.43, 58.69, 172–175 (broad due to 24 carboxylate and/or carboxylic acid groups). MS (FAB): 3,328 (M+H)+.

Analysis Calcualted for $C_{154}H_{268}N_{32}O_{68} \cdot 8[N(C_2H_5)_3] \cdot 17.20H_2O$: C, 50.81; H, 8.92; N, 11.73. Found: C, 50.33; H, 8.92; N, 11.75; H$_2$O, 6.10 (desorption Karl-Fisher).

E. [3aR-(3aα,3"aα,4β,4"β,5α,5"α,6β,6"b,7α,7"α,7aα, 7"aα)]-Dodecahydro-4,4",5,5",6,6",7,7"-octakis[[2-hydroxy-3-[(4,7,10-tricarboxymethyl)-1,4,7,10-tetraazacyclododecan-1-yl]propyl]oxy]dispiro-[1,3-benzodioxole-2,1'-cyclo-hexane-4',2"-[1,3]benzodioxole], Octagadolinium Salt Compound D (250 mg, 68.4 μmol as the octatriethylammonium salt) in water (5 mL) at pH 6.0 was treated with tetrahydrated gadolinium acetate (222 mg, 546 μmol) at 60° C. for 5 hours. The pH of the aqueous reaction mixture was maintained at 7.0±1.0. The resulting solution was then applied to a CHP-20P column (2.5×20 cm). The column was eluted with water (750 mL), 2.5% (300 mL), 5% (300 mL) and 10% (300 mL) of ethanol. The fractions containing the desired compound, which were eluted by 10% ethanol, were combined and concentrated in vacuo to obtain the octameric gadolinium chelate (200 mg) as a white solid in 60% yield.

Analysis Calculated for $C_{154}H_{244}N_{32}O_{68}Gd_8 \cdot 19.58H_2O \cdot 2.0C_2H_5OH$: C, 35.57; H, 5.58; N, 8.40. Found: C, 35.06; H, 6.22; N, 8.42; H$_2$O, 6.61% (desorption Karl-Fisher).

EXAMPLE 7

[2S-(2α,5α,8α,11α,)]-2,5,8,11-Tetramethyl-1,4,7,10-tetraazacyclododecane-1,4,7,10-tetraacetic Acid, Gadolinium Salt

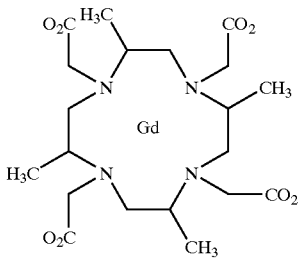

A. L-2-Benzylamino Propanol

To a solution of N-benzoyl-L-alanine (29.0 g, 150 mmol) in tetrahydrofuran (200 ml) at 0° C. was added a tetrahydrofuran solution of diborane (1 M solution, 800 ml) and the mixture was refluxed for 18 hours. Excess of diborane was decomposed with methanol and the solvents were removed under reduced pressure. The residue was dissolved in methanol (100 ml) and treated with 6 N hydrochloric acid (100 ml). The mixture was heated at 70° C. for 12 hours and the solvents were removed under reduced pressure. The residue was co-evaporated with methanol (5×150 ml) and the product was dissolved in water (50 ml), basified with 5 N sodium hydroxide to pH 12 and extracted with ethyl acetate (3×200 ml). The combined organic layers were washed with saturated sodium chloride (150 ml), dried and concentrated to a final volume of 100 ml. 300 ml of hexane was added and the solution cooled in the refrigerator overnight. The white crystalline needles deposited were collected and dried to afford pure compound A (41.4 g, yield 87%). m.p. 46–48° C.

B. (S)-1-Benzyl-2-methyl-ethyleneimine

To a solution of Compound A (33.0 g, 200 mmol) and triphenyl phosphine (79.66 g, 300 mmol) in ether (500 ml) stirred under nitrogen in an ice bath, was slowly added diethyl azo-dicarboxylate (95%, 50 ml, 300 mmol). The solution was stirred at room temperature for 16 hours. A crystalline precipitate (triphenylphosphine/diethyl hydrazine carboxylate complex) was filtered off and washed with hexane/ether (1:1, 200 ml). The ether solution was extracted with 1 N hydrochloric (2×100 ml). The hydrochloric solution was basified with 5N sodium hydroxide, extracted with ether (3×150 ml), dried and concentrated to afford the crude aziridine compound B as a yellow oily liquid. This was further purified by distillation under reduced pressure to afford pure compound B as a colorless liquid (24.3 g, yield 75%). b.p. 71–72° C. at 4 mm.

C. [2S-(2α,5α,8α,11α)]-2,5,8,11-Tetramethyl-1,4,7,10-tetrakis(phenylmethyl)-1,4,7,10-tetraazacyclododecane To a solution of compound B (19.1 g, 130 mmol) in ethanol (250 ml) was added p-toluenesulfonic acid (PTSA, 1.1 g, 6.5 mmol) and the mixture was stirred at room temperature for 64 hours. At the end of this time, an additional 1.1 g (6.5 mmol) of PTSA was added and the mixture was stirred for 48 hours. Ethanol was removed in vacuo, and the product was purified by column chromatography over silica gel (400 g) using methanol as the eluent. Fractions containing the pure product were combined, and solvent removal afforded 5.8 g of a salt. This was dissolved in methanol (100 mL) and basified with concentrated ammonia solution. The precipitated solid was filtered, dried and recrystallized from absolute ethanol to afford pure compound C as a colorless microcrystalline solid (2.8 g, yield 14%).
m.p.: 147–148° C.

D. [2S-(2α,5α,8α,11α,)]-2,5,8,11-Tetramethyl-1,4,7,10-tetraazacyclododecane

To a solution of compound C (2.35 g, 4 mmol) in ethyl acetate (40 mL) and ethanol (400 mL) was added ammonium formate (2.52 g) and palladium acetate on Carbon (20%, 2.35 g). The mixture was stirred under reflux for 16 hours. The solution was filtered to remove the catalyst and the solvents were removed to afford pure Compound D as a light yellow solid (840 mg, yield 92%).

E. [2S-(2α,5α,8α,11α)]-2,5,8,11-Tetramethyl-1,4,7,10-tetraazacyclododecane-1,4,7,10-tetraacetic Acid To a solution of compound D (570 mg, 2.5 mmol) in acetonitrile (200 mL) was added potassium carbonate (4.0 g) and t-butyl bromo acetate (2.34 g, 12 mmol). The mixture was stirred at room temperature for 18 hours. Potassium carbonate was filtered off, acetonitrile removed in vacuo and the residue purified by column chromatography over silica gel (50 g) using chloroform and methanol to afford the tetra butyl ester (1.6 g). This material was dissolved in trifluoroacetic acid (150 mL), anisole (10 mL) was added, and the mixture was stirred at room temperature for 16 hours. Trifluoroacetic acid was removed in vacuo and anisole was removed by co-evaporation with water (6×50 mL) to afford the crude product. The residue was dissolved in water (100 mL) and purified by anion exchange column chromatography over AG1-X2 resin (150 mL). The column, after washing with water, was eluted with 1 M formic acid. The fractions containing the pure product were combined. Solvent removal afforded the pure product. A small amount of formic acid that remained in the sample was removed by co-evaporation with water (5×50 mL) to obtain pure title compound as a colorless glassy solid (550 mg, yield 87%).

F. [2S-(2α,5α,8α,11α,)]-2,5,8,11-Tetramethyl-1,4,7,10-tetraazacyclododecane-1,4,7,10-tetraacetic Acid, Gadolinium Salt A sample of Compound E (0.1 g) was dissolved in 8 mL deionized water. 0.04 mL 5N sodium hyroxide (NaOH) was added to convert the ligand into the monosodium salt (reactant I). In a separate vial, 0.08 g of $GdCl_3$ powder was dissolved in 1 mL deionized water (reactant II). At about 70° C. and constant stirring, reactant II was added into reactant I dropwise over a time period of several hours. Meanwhile, 5N NaOH was pipetted into the solution from time to time to neutralize the protons released from chelation and maintain the reaction pH around 6. The excess metal ions were precipitated in the form of $M(OH)_3 \cdot xH_2O$ by raising solution pH to about 9.5 and incubating at both about 70° C. and room temperature for serveral hours. The precipitate was subsequently removed through centrifugation and filtration with a 0.22 $\mu m$ membrane. The filtrate was finally condensed and neutralized to pH 7 in preparation for HPLC purification.

The crude chelate product was purified by preparative HPLC, using mobile phase gradient ($CH_3CN:H_2O$) and silica-based reversed phase column (YMC C18, 5$\mu$, 120 A). The solvent was removed from fractions containing the desired product. The residue was dried in a vacuum oven at about 70° C. overnight, furnishing the chelate in 65% yield.

Mass Spectrum (FAB, m/e): $(Gd_{159}+Na)_+$ at 638. Elemental Analysis (C, H, N): Calculated for $C_{20}H_{33}N_4O_8GdNa \cdot 5.01H_2O$: C, 33.00; H, 5.96; N, 7.70%. Found: C, 32.94; H, 5.63; N, 7.75%

EXAMPLE 8

[αR-(aR*,α'R*,α"R*,α'"R*,2S*,5S*,8S*,11S*)]-α, α',α",a'",2,5,8,11-Octamethyl-1,4,7,10-tetraazacyclododecane-1,4,7,10-tetraacetic Acid, Gadolinium Salt

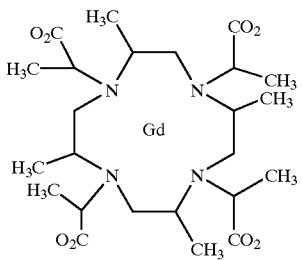

A. [αR-(aR*,α'R*,α"R*,α'"R*,2S*,5S*,8S*,11S*)]-α,α', α",a'",2,5,8,11-Octamethyl-1,4,7,10-tetraazacyclododecane-1,4,7,10-tetraacetic Acid To a solution of compound D from Example 7 (570 mg, 2.5 mmol) in acetonitrile (200 ml) was added potassium carbonate followed by L-benzyl-2-trifluoromethanesufonyloxy-propionate (prepared fresh from benzyl lactate as described in S. I. Kang et al., Inorganic Chem., 1993, 32, 2912–2918) (3.9 g, 12.5 mmol) and the mixture was stirred at room temperature for 48 hours. Potassium carbonate was filtered off, acetonitrile removed in vacuo and the residue purified by column chromatography over silica gel (100 g) using chloroform and the methanol to afford a tetra benzyl ester (1.1 g). This material was dissolved in a mixture of ethanol (75 ml) and water (10 ml) and hydrogenated over 10% Pd/C (250 mg) for 18 hours. The catalyst was filtered off and solvent removal afforded the crude product. This was dissolved in water (100 ml) and purified by anion exchange column chromatography over AG1-X2 resin (150 ml). The column, after washing with water, was eluted with a gradient of 0–200 mM formic acid. Fractions containing the pure product were combined. Solvent removal afforded the pure product. A small amount of formic acid that remained in the sample was removed by co-evaporation with water (5×50 ml) to obtain pure Compound A as a colorless glassy solid (340 mg, yield 26%).

B. [αR-(aR*,α'R*,α"R*,α'"R*,2S*,5S*,8S*,11S*)]-α,α', α",a'",2,5,8,11-Octamethyl-1,4,7,10-tetraazacyclododecane-1,4,7,10-tetraacetic Acid, Gadolinium Salt A sample of Compound A (0.15 g) was dissolved in 8 mL deionized water. 0.056 mL 5N NaOH was added to convert the ligand into the monosodium salt (reactant I). In a separate vial, 0.11 g of $GdCl_3$ powder was dissolved in 1 mL deionized water (reactant II). Reactants I and II were treated as described in the method of Example 7F to yield 74% of the title compound.

Mass Spectrum (FAB, m/e): $(Gd^{159}+Na)^+$ at 694. Elemental analysis: Calculated for $C_{24}H_{40}N_4O_8GdNa \cdot 1.98H_2O$: C, 39.57, H, 6.08, N, 7.69%. Found: C, 39.31, H, 6.19, N, 7.60%.

EXAMPLE 9

[2S-(2R*,5R*,8R*,11R*)]-2,5,8,11,-Tetramethyl-1,4,7,10-tetraazacylcododecane-1,4,7-triacetic Acid, Gadolinium Salt

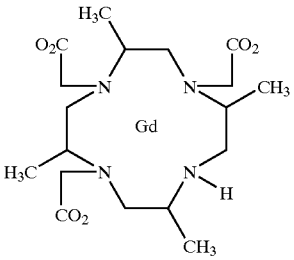

A. [2S-(2R*,5R*,8R*,11R*)]-2,5,8,11,-Tetramethyl-1,4,7,10-tetraazacyclododecane-1,4,7-triacetic Acid To a solution of Compound D (456 mg, 2 mmol) in acetonitrile (150 mL) was added sodium bicarbonate (4.0 g) and t-butyl bromo acetate (2.34 g, 12 mmol), and the mixture was stirred at room temperature for 48 hours. Sodium bicarbonate was filtered off, acetonitrile was removed in vacuo and the residue was dissolved in TFA (25 mL). Anisole (1 mL) was added and the mixture was stirred at room temperature for 12 hours. TFA was removed in vacuo and anisole was removed by co-evaporation with water (5×50 mL) to afford the crude product. The residue was dissolved in water (60 mL) and purified by anion exchange column chromatography over AG1-X2 resin (100 mL). The column, after washing with water, was eluted with a gradient of water to 50 mm M formic acid. The fractions were analyzed by HPLC and those containing the pure product were combined. Solvent removal afforded Compound A. A small amount of formic acid that remained in the sample was removed by co-evaporation with water (5×50 mL) to obtain pure Compound E as a colorless glassy solid (320 mg, yield 40%).

B. [2S-(2R*,5R*,8R*,11R*)]-2,5,8,11,-Tetramethyl-1,4,7,10-tetraazacylcododecane-1,4,7-triacetic Acid, Gadolinium Salt A sample of Compound A (0.125 g) was dissolved in 9 mL deionized water (reactant I). In a separate vial, 0.129 g of $GdCl_3$ powder was dissolved in 1.5 mL deionized water (reactant II). Reactants I and II were treated as described in the method of Example 7F to yield 80% of the title compound.

Mass Spectrum (FAB, m/e): $(Gd^{159}+H)^+$ at 559. Elemental Analysis (C, H, N): Calculated for $C_{18}H_{31}N_4O_6Gd \cdot 2.81H_2O$: C, 35.60, H, 6.08, N, 9.22%. Found: C, 35.65, H, 6.11, N, 9.02%.

EXAMPLE 10

10-(Phosphonomethyl)-1,4,7,10-tetraazacyclododecane-1,4,7-triacetic Acid, Gadolinium Salt

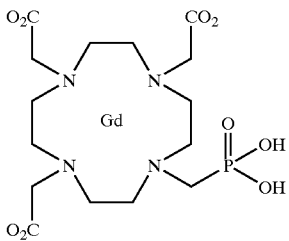

A. 10-(Phosphonomethyl)-1,4,7,10-tetraazacyclododecane-1,4,7-triacetic Acid

A mixture of DO3A (1 g, 2.89 mmol), phosphorus acid (0.485 g, 5.91 mmol), concentrated hydrochloric acid (1.1 mL, 13.4 mmol) and formaldehyde (1.35 mL of 37% aqueous solution, 16.4 mmol) in water (2.5 mL) was refluxed for 27.5 hours. Removal of water from the reaction mixture in vacuo gave an off-white solid (1.74 g) as a crude product of Compound A. The solid was dissolved in water (50 mL), and the pH of the resulting solution was adjusted to 5.0 by addition of 1.0 N sodium hydroxide. The aqueous solution was applied to a strong cation exchange column of AG50WX8 (250 mL, flowrate, 12.5 mL/minute). Initially, water was used to remove any negatively charged inorganic species, and ammonium hydroxide (1.0 M) was employed to bring out the crude product. After removal of the ammonium hydroxide from the fractions containing the product, the residue dissolved in 5mM TEAB (pH 7.5) was applied to a DEAE Sephadex ion exchange column (750 mL, flowrate, 4 mL/minute). The column was eluted with TEAB, whose concentration varied from 5 to 400 mM. The concentration of the buffer was doubled at every column volume (1 L): 5, 10, 20, 40, 67, 80, 100, 125, 200 and 400 mM. Compound A required 400 mM TEAB to be brought out from the column. Evaporation of the buffer from the fractions containing Compound A gave a white residue (0.9 g). The solid, dissolved in water (35 mL) was loaded on a strongly basic-anion column of Amberlite IRA 900 C (200 mL, flowrate, 14 mL/minute). Water was first used to remove triethylamine followed by sulfuric acid (1M) to elute Compound A from the column. The fractions containing the product were combined and applied to a column of Reillex 425 poly(4-vinyl)pyridine (PVP) 250 mL, 10 mL/minute). Water was used to elute the product free from sulfuric acid. Removal of water from the eluate (3.7 L) yielded Compound A (0.6 g, 47%) as a dense solid.

B. 10-(Phosphonomethyl)-1,4,7,10-tetraazacyclododecane-1,4,7-triacetic Acid, Gadolinium Salt A sample of Compound A (0.2 g) was dissolved in 5 mL deionized water and its pH was adjusted to 4 with dilute NaOH. 0.096 g of $Gd_2O_3$ powder was added slowly. The solution was refluxed overnight. The excess metal ions were precipitated in the form of $M(OH)_3 \cdot xH_2O$ by raising solution pH to about 9.5 with 1N NaOH and incubating at both about 70° C. and room temperature for several hours. The precipitate was subsequently removed through centrifugation and filtration with 0.22 μm membrane. The filtrate was finally condensed and neutralized to pH 7 with 1N HCl in preparation for HPLC purification. HPLC purification was performed as in Example 7F to yield 64% of the title compound.

Mass Spectrum (FAB, m/e): $(Gd^{159}+2Na-H)^+$ at 640.
Elemental Analysis (C, H, N): Calculated for $C_{15}H_{24}N_4O_9PGdNa_2 \cdot 2.59H_2O$: C, 26.29, H, 4.29, N, 8.18%. Found: C, 26.23, H, 4.18, N, 7.93%.

What is claimed is:

1. A compound of the following formula I:

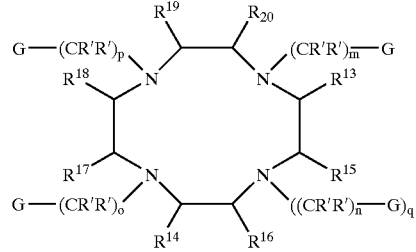

wherein
each m, n, o and p is independently 1 or 2;
q is 0 or 1;
each G is independently —COOR", —P(O)(OR")$_2$, —P(O)(OR")$_2$, —P(O)(OR")(R") or —C(O)N(R")$_2$;
each R' is independently hydrogen or alkyl, alkoxy, cycloalkyl, hydroxyalkyl or aryl, each of which is optionally substituted, or a functional group that forms a conjugate with a biomolecule or that forms a multimer of said compound of formula I;
wherein said biomolecule is selected from the group consisting of peptides, polypeptides, oligosaccharides or fragments thereof; proteins, including monoclonal antibodies; lipids; sugars; alcohols; bile acids; fatty acids; amino acids; RNA, DNA, or their modified fragments; or other biomolecules that act as receptor binding ligands;
each R" is hydrogen;
each $R^{13}$ through $R^{20}$ is independently hydrogen, alkyl, hydroxyalkyl, alkoxyalkyl or a functional group that forms a conjugate with a biomolecule or that forms a multimer of said compound of formula I;
or $R^{13}$ together with $R^{15}$, and $R^{17}$ together with $R^{18}$, independently form, together with the carbon atoms in the tetraazacyclododecane macrocycle to which they are attached, a fused fully or partially saturated cyclohexyl ring which may be unsubstituted or substituted by one or more halogen, alkyl, ether, hydroxy or hydroxyalkyl groups, and which may be further fused to a carbocyclic ring, or $R^{13}$ and $R^{15}$, are each hydrogen and $R^{17}$, together with $R^{18}$, forms a fused fully or partially saturated cyclohexyl ring as defined above, or $R^{13}$, together with $R^{15}$, forms a fused fully or partially saturated non-aromatic cyclohexyl ring as defined above and $R^{17}$ and $R^{18}$ are hydrogen; provided that (a.) when G is always —COOR" and (i.) R', R", $R^{14}$ and $R^{16}$ through $R^{20}$ are all hydrogen, then $R^{13}$ and $R^{15}$ are other than hydrogen; (ii.) R" and $R^{13}$ through $R^{20}$ are all hydrogen, and m, n, o, p and q are each 1, then (CR'R') is other than (CH$_2$) and (CHCH$_3$); (iii.) R', R", $R^{13}$, $R^{14}$, $R^{17}$ and $R^{20}$ are all hydrogen, then at least two of $R^{15}$, $R^{16}$, $R^{18}$ and $R^{19}$ are other than methyl; and (iv.) R", $R^{16}$, $R^{19}$ and $R^{20}$ are all hydrogen, and each (CR'R') is independently (CHR') or (CH$_2$CHR'), then $R^{13}$ and $R^{15}$, and $R^{17}$ and $R^{18}$, are other than a fused ring; and (b.) when G is always —P(O)(OR")$_2$, —P(O)(OR")(R") or —C(O)N(R")$_2$, then at least one R' or $R^{13}$ through $R^{20}$ is other than hydrogen;
or a salt or multimeric form thereof.

2. A metal chelate, comprising a compound of claim 1 complexed with a metal atom.

3. The chelate of claim 2, wherein the metal is selected from atoms having an atomic number of 21 to 29, 42 or 57 to 83.

4. The chelate of claim 3, wherein said metal is gadolinium.

5. A compound of the following formula II:

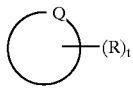

wherein
Q is a 4- to an 8-membered carbocyclic ring which may be fully or partially saturated;

t is an integer from 2 to 16;

each R group is independently hydrogen, —OH, —CH$_2$—A, —OCH$_2$CH(OH)CH$_2$—A or a functional group that forms a conjugate with a biomolecule, provided that at least two of the R groups are selected from —CH$_2$—A or —OCH$_2$CH(OH)CH$_2$—A;

wherein said biomolecule is selected from the group consisting of peptides, polypeptides, oligosaccharides or fragments thereof; proteins, including monoclonal antibodies; lipids; sugars; alcohols; bile acids; fatty acids; amino acids; RNA, DNA, or their modified fragments; or other biomolecules that act as receptor binding ligands; and A is a moiety capable of chelating a metal atom.

6. A compound of claim 5 wherein A is

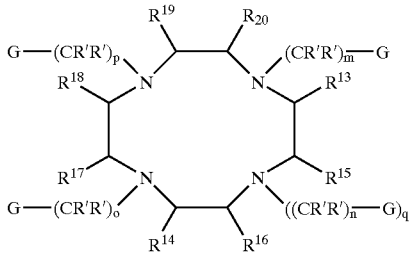

each m, n, o and p is independently 1 or 2;

q is 0 or 1;

each G is independently —COOR", —P(O)(OR")$_2$, —P(O)(OR")(R") or —C(O)N(R")$_2$;

each R' is independently hydrogen or alkyl, alkoxy, cycloalkyl, hydroxyalkyl or aryl, each of which is optionally substituted, or a functional group that forms a conjugate with a biomolecule or that forms a multimer;

each R" is hydrogen;

each R$^{13}$ through R$^{20}$ is independently hydrogen, alkyl, hydroxyalkyl, alkoxyalkyl or a functional group that forms a conjugate with a biomolecule or that forms a multimer of said compound of the formula I;

or R$^{13}$ together with R$^{15}$, and R$^{17}$ together with R$^{18}$, independently form, together with the carbon atoms in the tetraazacyclododecane macrocycle to which they are attached, a fused fully or partially saturated cyclohexyl ring which may be unsubstituted or substituted by one or more halogen, alkyl, ether, hydroxy or hydroxyalkyl groups, and which may be further fused to a carbocyclic ring, or R$^{13}$ and R$^{15}$ are each hydrogen and R$^{17}$, together with R$^{18}$, forms a fused fully or partially saturated cyclohexyl ring as defined above, or R$^{13}$, together with R$^{15}$, forms a fused fully or partially saturated cyclohexyl ring as defined above and R$^{17}$ and R$^{18}$ are hydrogen; provided that (a.) when G is always —COOR" and (i.) R', R", R$^{14}$ and R$^{16}$ through R$^{20}$ are all hydrogen, then R$^{13}$ and R$^{15}$ are other than hydrogen; (ii.) R" and R$^{13}$ through R$^{20}$ are all hydrogen, and m, n, o, p and q are each 1, then (CR'R') is other than (CH$_2$) and (CHCH$_3$); (iii.) R', R", R$^{13}$, R$^{14}$, R$^{17}$ and R$^{20}$ are all hydrogen, then at least two of R$^{15}$, R$^{16}$, R$^{18}$ and R$^{19}$ are other than methyl; and (iv.) R", R$^{16}$, R$^{19}$ and R$^{20}$ are all hydrogen, and each (CR'R') is independently (CHR') or (CH$_2$CHR'), then R$^{13}$ and R$^{15}$, and R$^{17}$ and R$^{18}$, are other than a fused ring; and (b.) when G is always —P(O)(OR")$_2$, —P(O)(OR")(R") or —C(O)N(R")$_2$, then at least one R' or R$^{13}$ through R$^{20}$ is other than hydrogen;

or a salt or multimeric form thereof.

7. A compound of claim 5, wherein A is

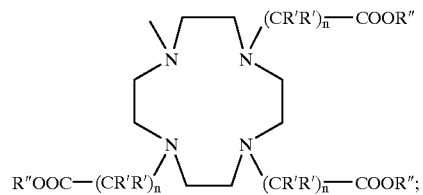

each R' is independently hydrogen, alkyl, alkoxy, hydroxyalkyl, aryl, aralkyl or arylalkoxy;

each R" is hydrogen; and each n is 1 or 2.

8. A compound of claim 5 wherein

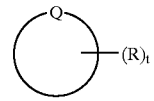

is

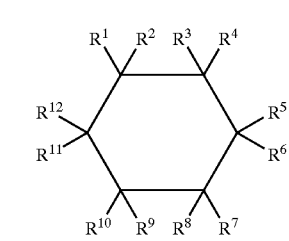

each R$^1$ through R$^{12}$ group is independently hydrogen, —OH, —CH$_2$—A, —OCH$_2$CH(OH)CH$_2$—A or a functional group that forms a conjugate with a biomolecule;

at least two of R$^1$ through R$^{12}$ are selected from —CH$_2$—A or —OCH$_2$CH(OH)CH$_2$—A; and R$^8$ and R$^9$ taken together may additionally form the group —O—[C(RR)]—O— where each R is independently hydrogen or alkyl, or R$^8$ and R$^9$ taken together may form 9. A compound of claim 6 wherein

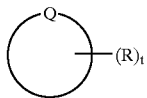

is a compound of the formula

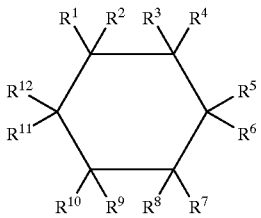

wherein each $R^1$ through $R^{12}$ group is independently hydrogen, —OH, —CH$_2$—A, —OCH$_2$CH(OH)CH$_2$—A or a functional group that forms a conjugate with a biomolecule;

at least two of $R^1$ through $R^{12}$ are selected from —CH$_2$—A or —OCH$_2$CH(OH)CH$_2$—A; and $R^8$ and $R^9$ taken together may additional form the group —O—[C(RR)]—O— where each R is independently hydrogen or alkyl, or $R^8$ and $R^9$ taken together may form

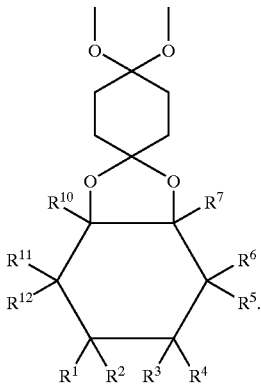

10. A compound of claim 7, wherein

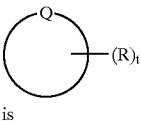

is

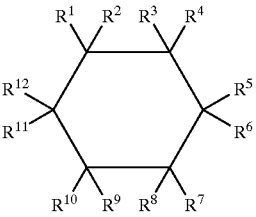

each $R^1$ through $R^{12}$ group is independently hydrogen, —OH, —CH$_2$—A, —OCH$_2$CH(OH)CH$_2$—A or a functional group that forms a conjugate with a biomolecule;

at least two of $R^1$ through $R^{12}$ are selected from —CH$_2$—A or —OCH$_2$CH(OH)CH$_2$—A; and $R^8$ and $R^9$ taken together may additionally form the group —O—[C(RR)]—O— where each R is independently hydrogen or alkyl, or $R^8$ and $R^9$ taken together may form

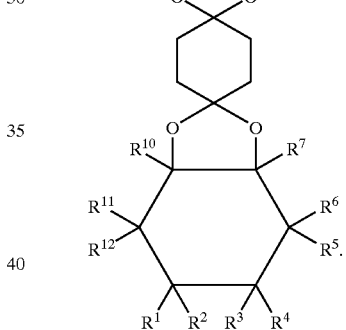

11. A metal chelate, comprising a compound of claim 5 complexed with a metal atom.

12. A metal chelate, comprising a compound of claim 6 complexed with a metal atom.

13. A compound selected from the group consisting of:

(1α,2α,4β,5β)-10,10'-[(1,2,4,5-Tetrahydroxy-1,4-cyclohexanediyl)bis(methylene)]bis[1,4,7,10-tetraazacyclododecane-1,4,7-triacetic acid];

(3aα,4α,5β,6α,7β,7aα)-10,10',10'',10'''-[[Hexahydro-2,2-dimethyl-1,3-benzodioxol-4,5,6,7-tetrayl]tetra(oxy)-tetra(2-hydroxy-3,1-propanediyl)]tetrakis[1,4,7,10-tetraazacyclododecane-1,4,7-triacetic acid];

3,4,5,6-Tetra-O-[2-hydroxy-3-[4,7,10-tris(carboxymethyl)-1,4,7,10-tetraazacyclododecan-1-yl]propyl]-myo-inositol;

(1α,2α,3α,4β,5α,6β)-10,10'-[(2,3,5,6-tetrahydroxy-1,4-cyclohexanediyl)bis(2-hydroxy-3,1-propanediyl)]bis[1,4,7,10-tetraazacyclododecane-1,4,7-triacetic acid];

10-[[1,4-Dihydroxy-2,5-bis[2-hydroxy-3-[4,7,10-tris-(carboxymethyl)-1,4,7,10-tetraazacyclododecan-1-yl]-propoxy]-4-[[4,7,10-tris(carboxymethyl)-1,4,7,10-tetraazacyclododecan-1-yl]methyl]cyclohexyl]methyl]-1,4,7,10-tetraazacyclododecane-1,4,7-triacetic acid;

[3aR-(3aα,3"aα,4β,4"β,5α,5"α,6β,6"b,7α,7"α,7aα,7"aα)]-dodecahydro-4,4",5,5",6,6",7,7"-octakis-[[2-hydroxy-3-[(4,7,10-tricarboxymethyl)-1,4,7,10-tetraazacyclododecan-1-yl]propyl]-oxy]dispiro-[1,3-benzodioxole-2,1'-cyclo-hexane-4',2"-[1,3]-benzodioxole];

[2S-(2α,5α,8α,11α)]-2,5,8,11-Tetramethyl-1,4,7,10-tetraazacyclododecane-1,4,7,10-tetraacetic acid;

[αR-(aR*,α'R*,α"R*,α'"R*,2S*,5S*,8S*,11S*)]-α,-α',α",a'",2,5,8,11-octamethyl-1,4,7,10-tetraazacyclododecane-1,4,7,10-tetraacetic acid;

[2S-(2R*,5R*,8R*,11R*)]-2,5,8,11,-Tetramethyl-1,4,7,10-tetraazacylcododecane-1,4,7-triacetic acid; and 10-(Phosphonomethyl)-1,4,7,10-tetraazacyclododecane-1,4,7-triacetic acid.

14. A compound selected from the group consisting of:

(1α,2α,4β,5β)-10,10'-[(1,2,4,5-Tetrahydroxy-1,4-cyclohexanediyl)bis(methylene)]bis[1,4,7,10-tetraazacyclododecane-1,4,7-triacetic acid], digadolinium salt;

(3aα,4α,5β,6α,7β,7aα)-10,10',10",10'"-[[Hexahydro-2,2-dimethyl-1,3-benzodioxol-4,5,6,7-tetrayl]tetra(oxy)-tetra(2-hydroxy-3,1-propanediyl)]tetrakis[1,4,7,10-tetraazacyclododecane-1,4,7-triacetic acid], tetragadolinium salt;

3,4,5,6-Tetra-O-[2-hydroxy-3-[4,7,10-tris(carboxymethyl)-1,4,7,10-tetraazacyclododecan-1-yl]propyl]-myo-inositol, tetragadolinium salt;

(1α,2α,3α,4β,5α,6β)-10,10'-[(2,3,5,6-tetrahydroxy-1,4-cyclohexanediyl)bis(2-hydroxy-3,1-propanediyl)]bis[1,4,7,10-tetraazacyclododecane-1,4,7-triacetic acid], digadolinium salt;

10-[[1,4-Dihydroxy-2,5-bis[2-hydroxy-3-[4,7,10-tris-(carboxymethyl)-1,4,7,10-tetraazacyclododecan-1-yl]-propoxy]-4-[[4,7,10-tris(carboxymethyl)-1,4,7,10-tetraazacyclododecan-1-yl]methyl]cyclohexyl]methyl]-1,4,7,10-tetraazacyclododecane-1,4,7-triacetic acid, tetragadolinium salt;

[3aR-(3aα,3"aα,4β,4"β,5α,5"α,6β,6"b,7α,7"α,7aα,7"aα)]-dodecahydro-4,4",5,5",6,6",7,7"-octakis-[[2-hydroxy-3-[(4,7,10-tricarboxymethyl)-1,4,7,10-tetraazacyclododecan-1-yl]propyl]-oxy]dispiro-[1,3-benzodioxole-2,1'-cyclo-hexane-4',2"-[1,3]-benzodioxole], octagadolinium salt;

[2S-(2α,5α,8α,11α,)]-2,5,8,11-Tetramethyl-1,4,7,10-tetraazacyclododecane-1,4,7,10-tetraacetic acid, gadolinium salt;

[αR-(aR*,α'R*,α"R*,α'"R*,2S*,5S*,8S*,11S*)]-α,α',α",a'",2,5,8,11-Octamethyl-1,4,7,10-tetraazacyclododecane-1,4,7,10-tetraacetic acid, gadolinium salt;

[2S-(2R*,5R*,8R*,11R*)]-2,5,8,11,-Tetramethyl-1,4,7,10-tetraazacylcododecane-1,4,7-triacetic acid, gadolinium salt; and 10-(Phosphonomethyl)-1,4,7,10-tetraazacyclododecane-1,4,7-triacetic acid, gadolinium salt.

* * * * *